United States Patent
Um et al.

(10) Patent No.: US 10,125,344 B2
(45) Date of Patent: Nov. 13, 2018

(54) APPARATUS AND METHOD FOR BIOENERGY PRODUCTION USING REGENERATED ACID SOLUTION

(71) Applicant: KOREA INSTITUTE OF SCIENCE AND TECHNOLOGY, Seoul (KR)

(72) Inventors: Young Soon Um, Seoul (KR); Hong Gon Kim, Seoul (KR); Byoung Sung Ahn, Seoul (KR); Sang Deuk Lee, Seoul (KR); Chang Soo Kim, Seoul (KR); Dong Jin Suh, Seoul (KR); Kyung Min Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 115 days.

(21) Appl. No.: 15/329,399

(22) PCT Filed: Sep. 21, 2015

(86) PCT No.: PCT/KR2015/009880
§ 371 (c)(1),
(2) Date: Jan. 26, 2017

(87) PCT Pub. No.: WO2016/052896
PCT Pub. Date: Apr. 7, 2016

(65) Prior Publication Data
US 2017/0218322 A1    Aug. 3, 2017

(30) Foreign Application Priority Data
Oct. 1, 2014    (KR) ................ 10-2014-0132605

(51) Int. Cl.
| C12M 1/00 | (2006.01) |
| C12M 1/02 | (2006.01) |
| C12M 1/34 | (2006.01) |

(52) U.S. Cl.
CPC ............ *C12M 45/06* (2013.01); *C12M 23/34* (2013.01); *C12M 27/00* (2013.01); *C12M 29/18* (2013.01); *C12M 41/12* (2013.01); *C12M 41/28* (2013.01)

(58) Field of Classification Search
CPC ...... C12M 23/14; C12M 23/42; C12M 37/00; C12M 37/04; C12M 23/48; C12M 23/28; C12M 41/00
See application file for complete search history.

(56) References Cited

U.S. PATENT DOCUMENTS

| 8,530,695 B2 * | 9/2013 | Reunanen et al. ...... C07C 51/44 549/489 |
| 2013/0157333 A1 * | 6/2013 | Tetarenko et al. ........ C12P 7/14 435/162 |

(Continued)

FOREIGN PATENT DOCUMENTS

| JP | 2012-183031 A | 9/2012 |
| KR | 1020110081518 A | 7/2011 |

(Continued)

OTHER PUBLICATIONS

Young-Jun Seo, Bioethanol production from waste mushroom medium byoxalic acid pretreatment and oxalic acid recovery, A master's thesis for Young-Jun Seo in the Department of Forest Products and Technology Graduate School Chonnam National University, Feb. 2013.

*Primary Examiner* — Gautam Prakash
(74) *Attorney, Agent, or Firm* — Goldilocks Zone IP Law

(57) ABSTRACT

The apparatus includes: a pretreatment tank where biomass and a first acid solution are stirred to extract sugar components from the biomass; a hydrolysis tank where water is added to the pretreated mixture transferred from the pretreatment tank such that the concentration of the acid is reduced and the sugar components are hydrolyzed to pro- (Continued)

duce an acid hydrolyzate; a first sugar-acid separation tank where the acid hydrolyzate is separated into a second acid solution and a first hydrolyzate; a second sugar-acid separation tank where the first hydrolyzate is separated into a third acid solution and a second hydrolyzate; a fermentation tank where the second hydrolyzate is fermented to produce bioenergy; and an acid solution concentration tank where a mixture of the second acid solution transferred from the first sugar-acid separation tank and the third acid solution transferred from the second sugar-acid separation tank is concentrated to a higher level for reuse.

17 Claims, 14 Drawing Sheets

(56) References Cited

U.S. PATENT DOCUMENTS

| | | | | |
|---|---|---|---|---|
| 2013/0236941 | A1* | 9/2013 | Burns-Guydish et al. | ................... C12N 1/14 435/165 |
| 2014/0234936 | A1* | 8/2014 | Kusuda et al. | ........... C12P 7/10 435/165 |
| 2016/0108355 | A1* | 4/2016 | Nishino et al. | .......... C13K 1/02 435/303.1 |

FOREIGN PATENT DOCUMENTS

| | | | |
|---|---|---|---|
| KR | 1020130008894 A | 1/2013 | |
| KR | 1020130046067 A | 5/2013 | |

\* cited by examiner

[Fig. 1]
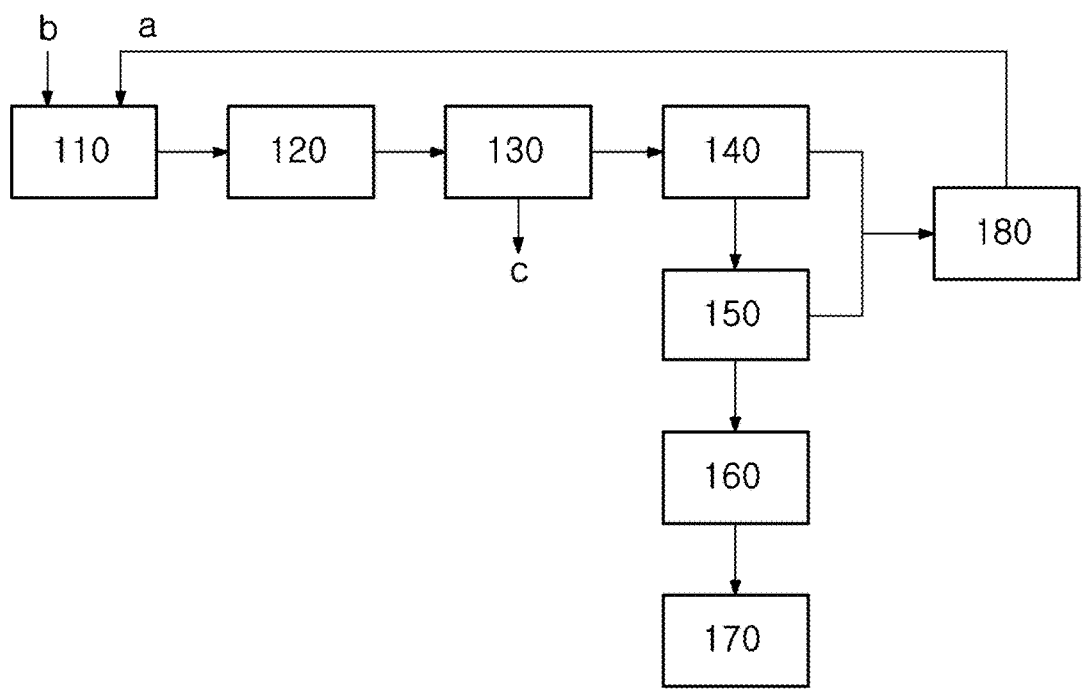

[Fig. 2]
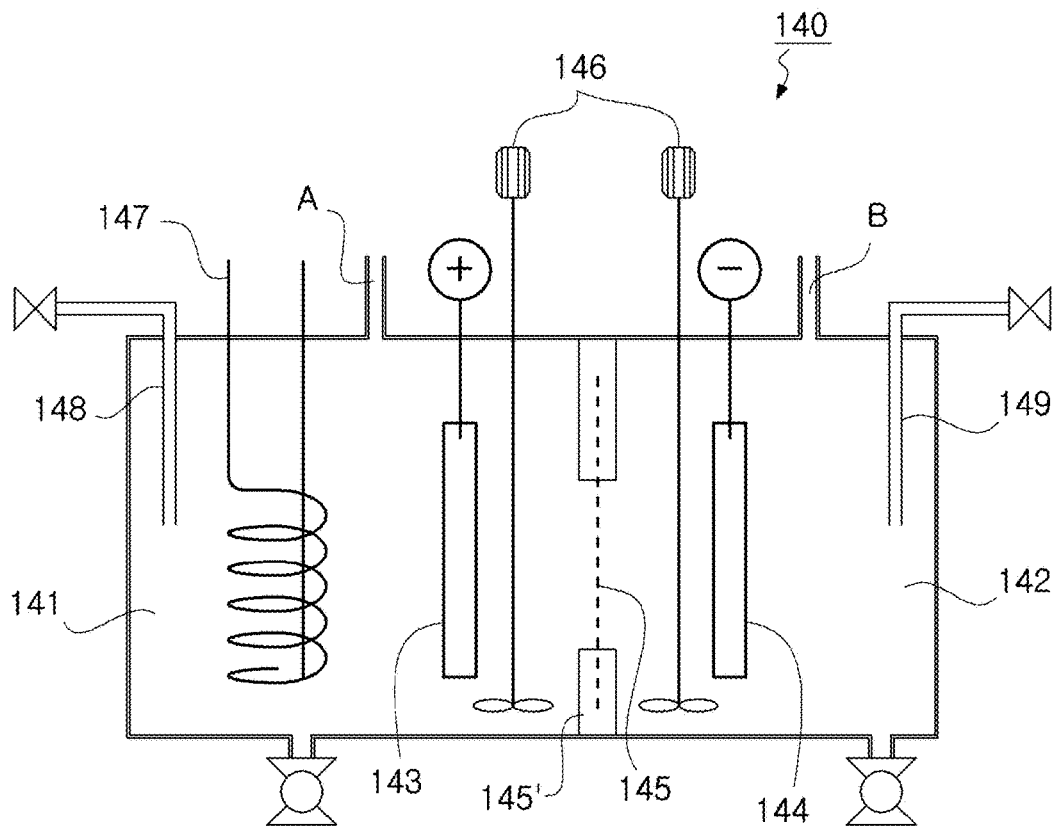
[Fig. 3a]
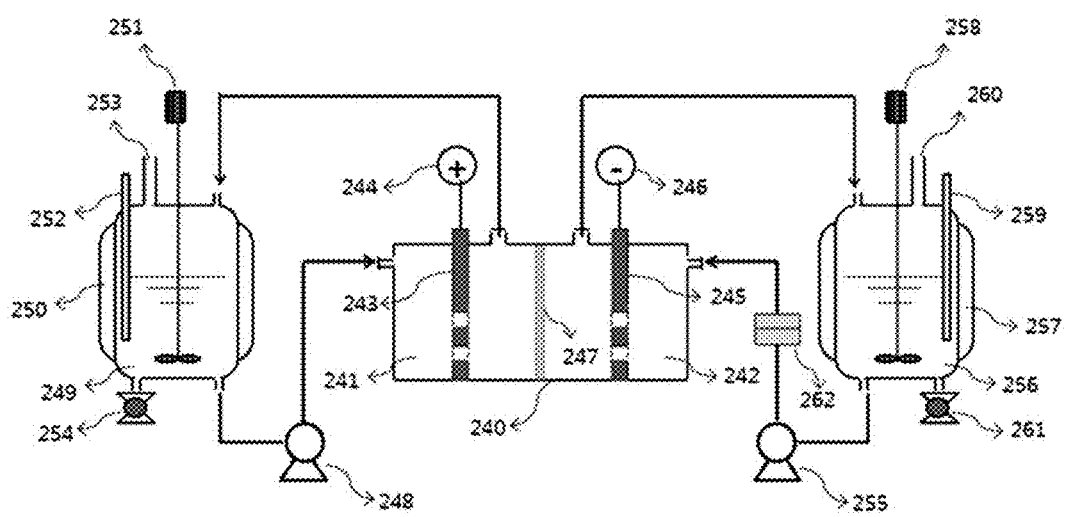

[Fig. 3b]
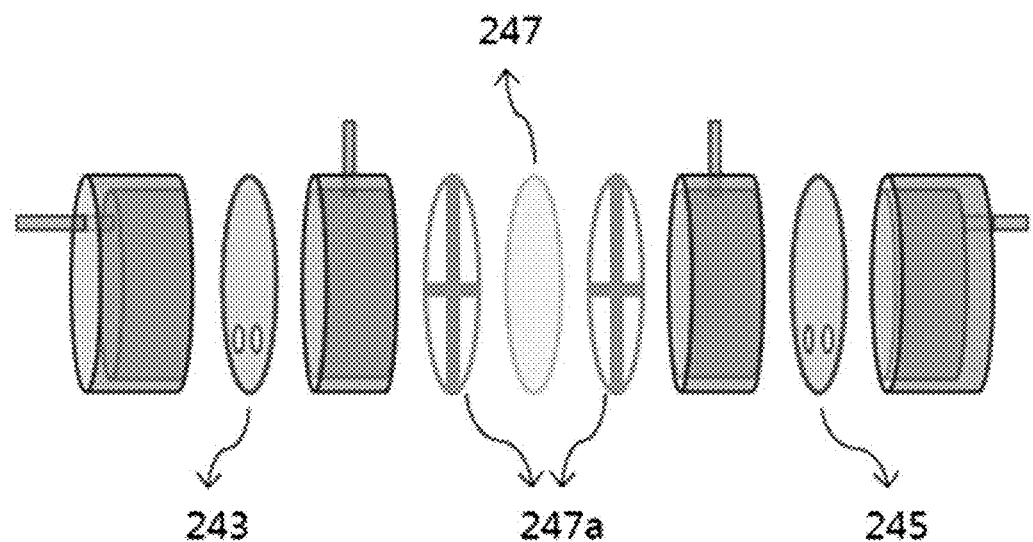
[Fig. 3c]
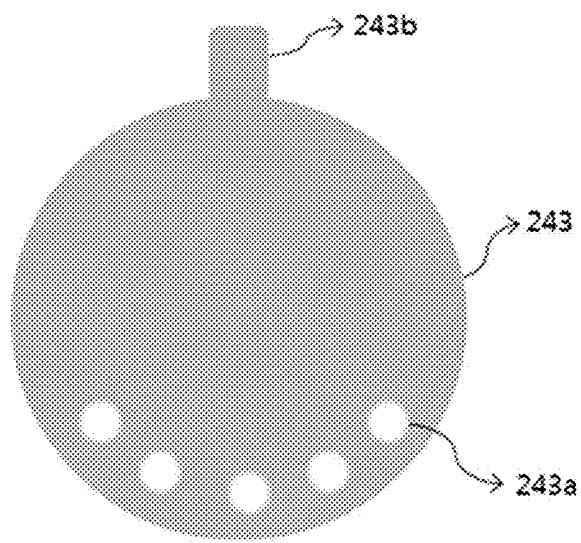

[Fig. 4a]
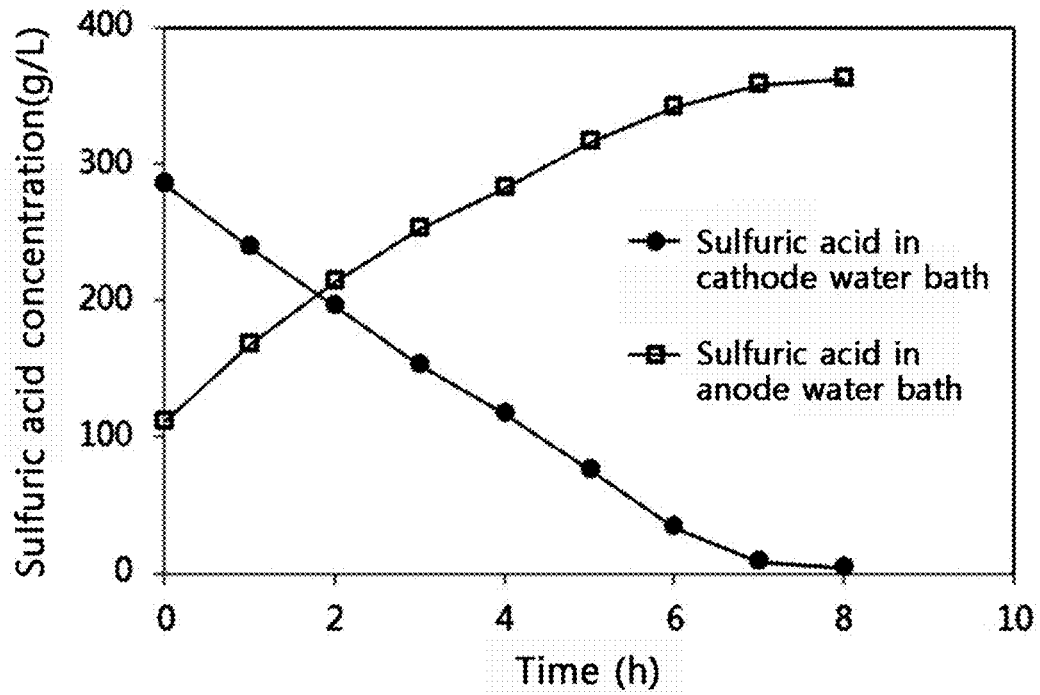
[Fig. 4b]
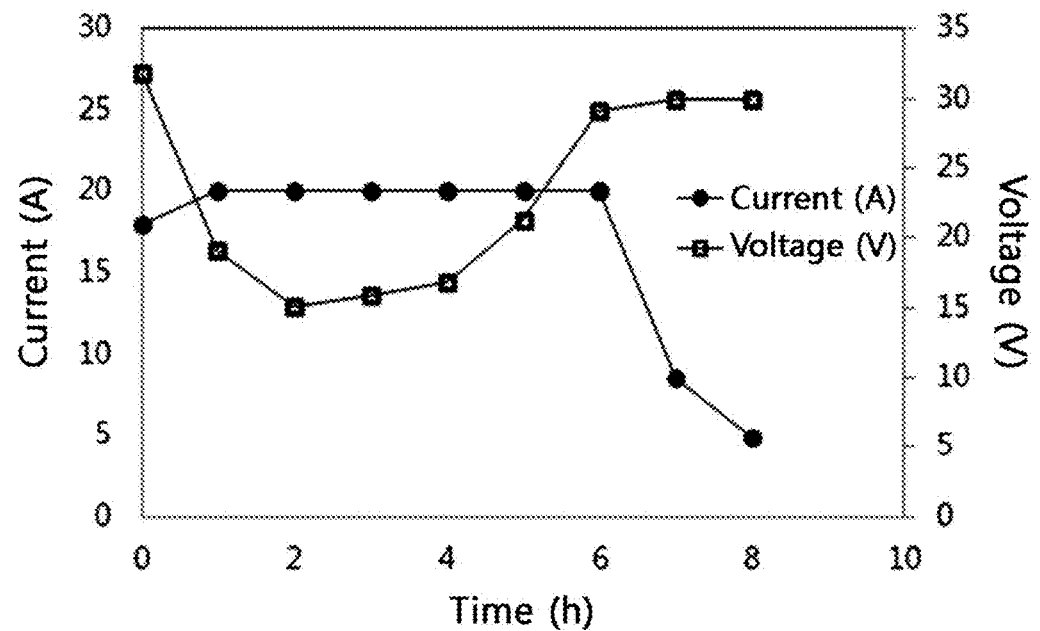

[Fig. 4c]
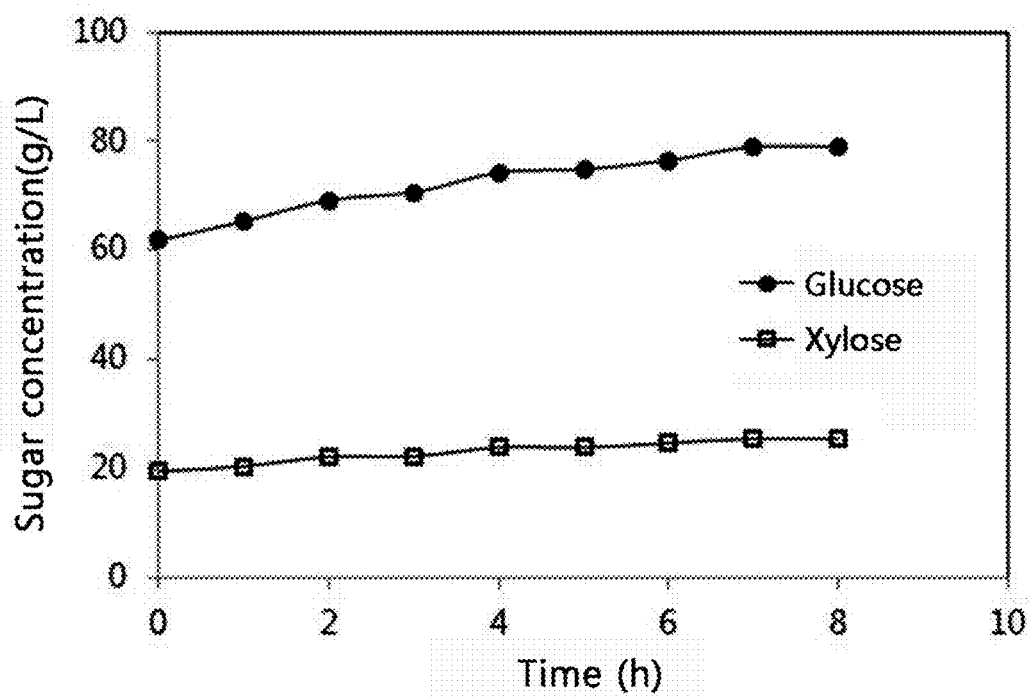
[Fig. 5a]
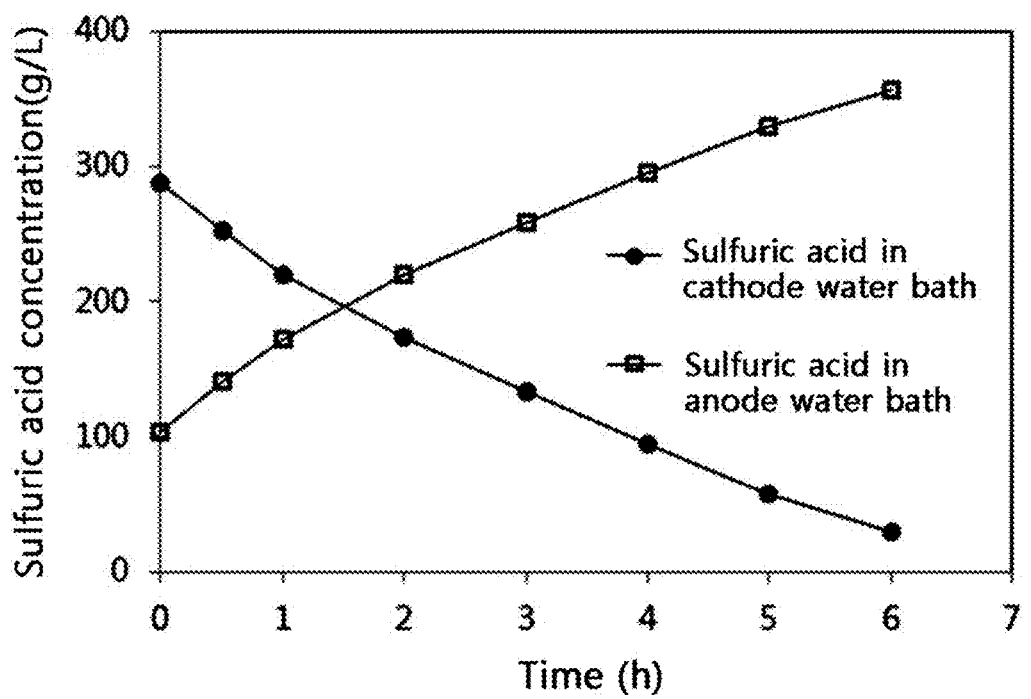

[Fig. 5b]
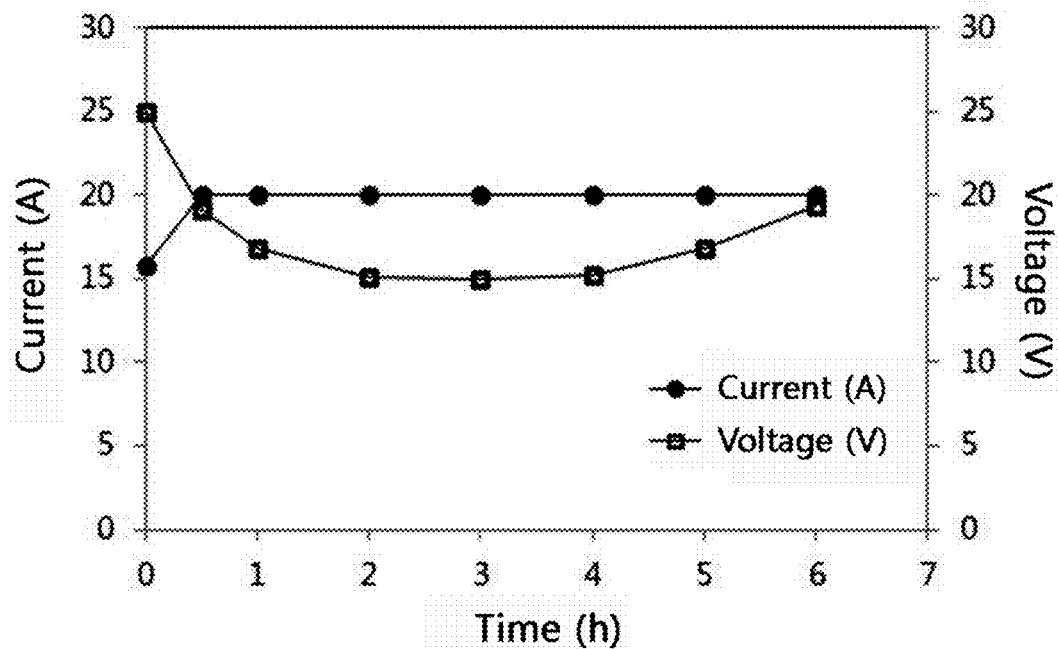
[Fig. 5c]
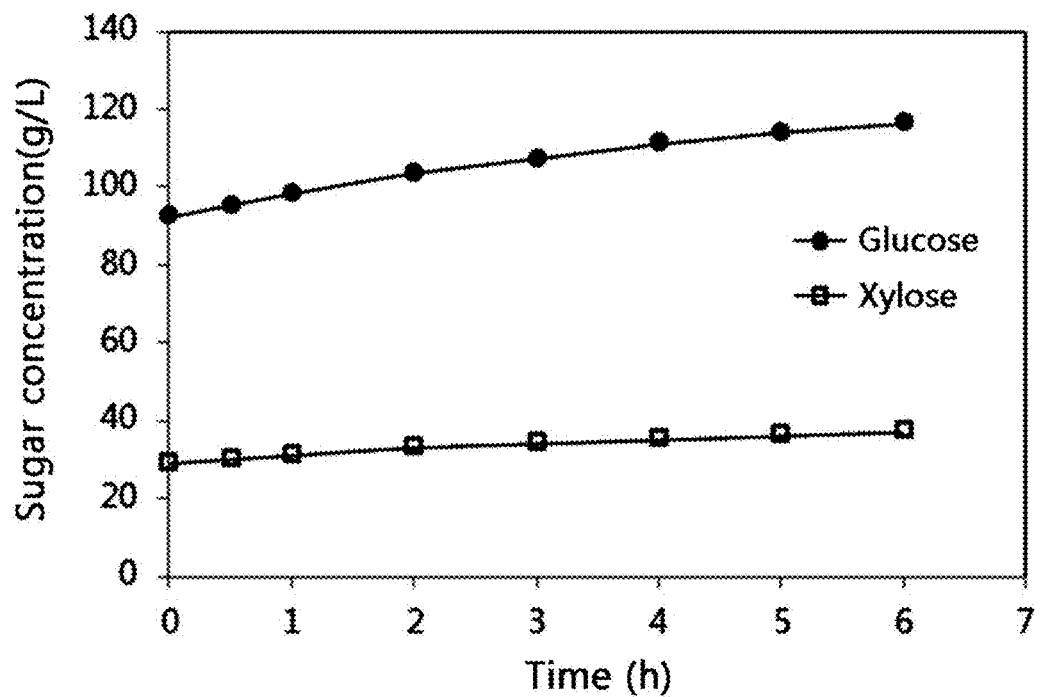

[Fig. 6a]
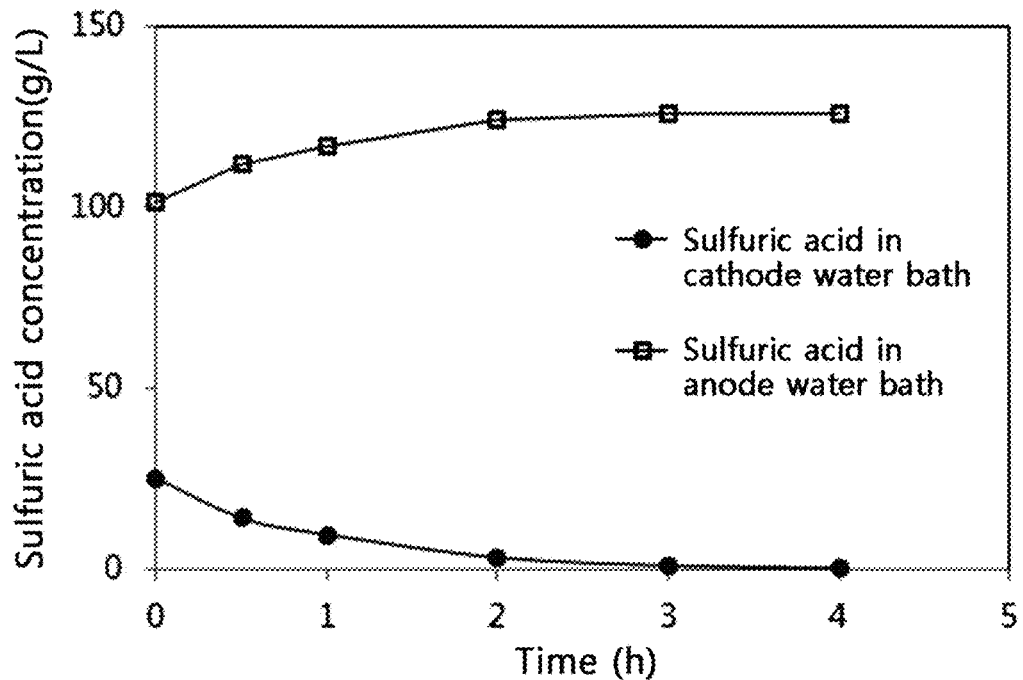
[Fig. 6b]
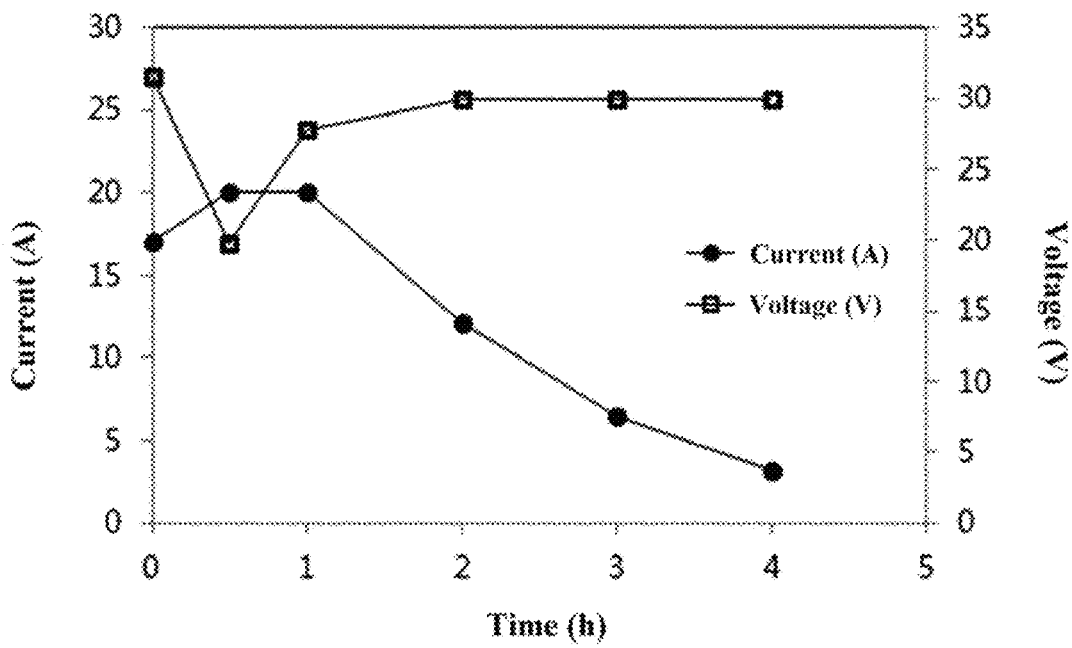

[Fig. 6c]
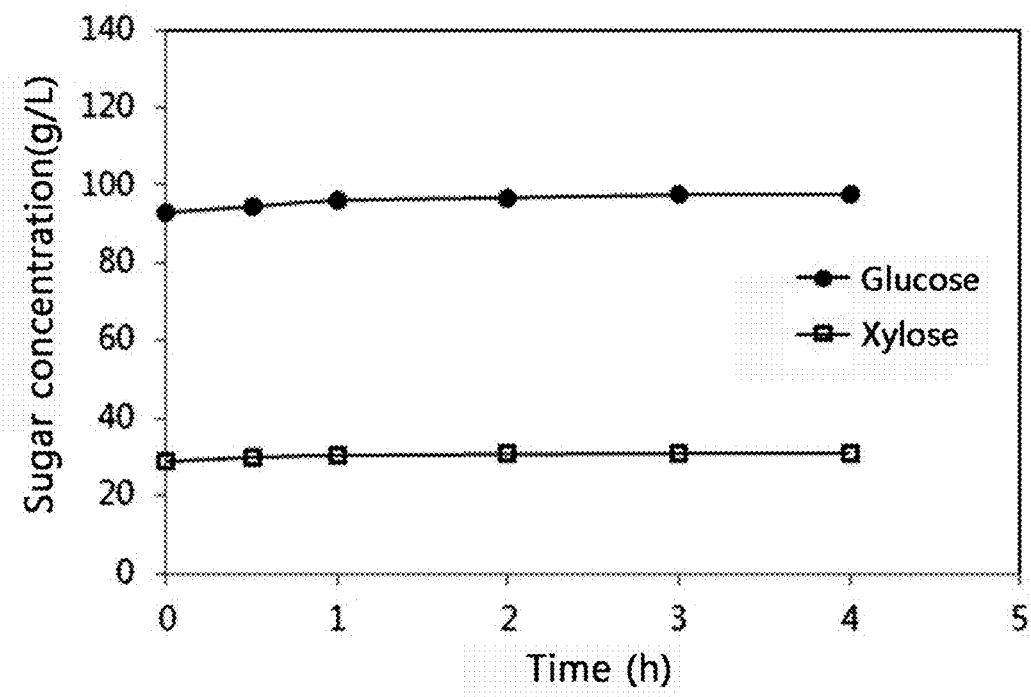
[Fig. 7a]
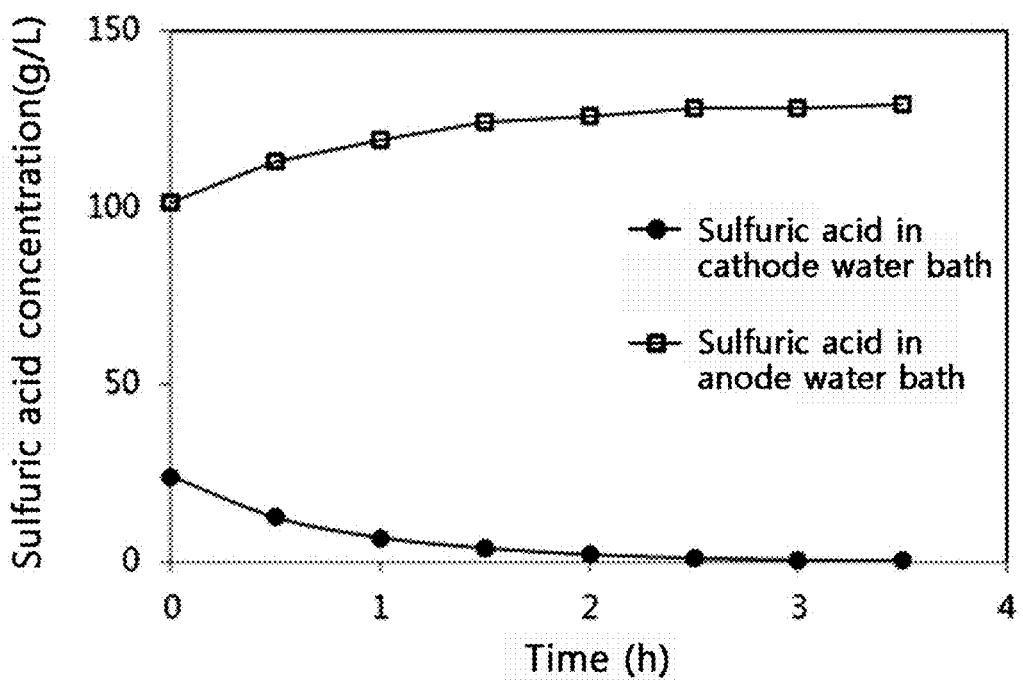

[Fig. 7b]
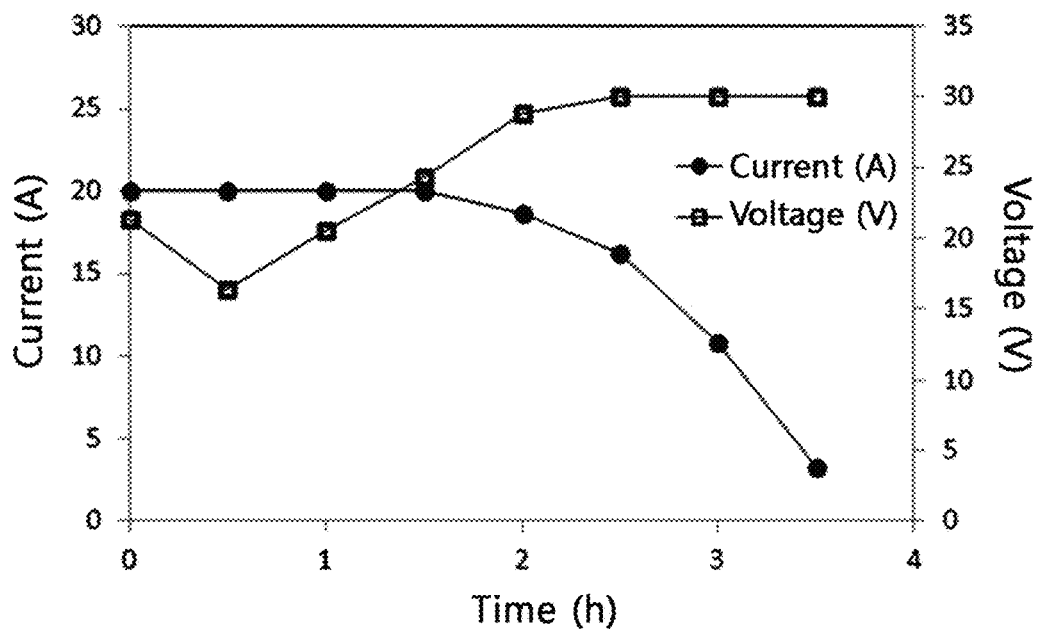
[Fig. 8a]
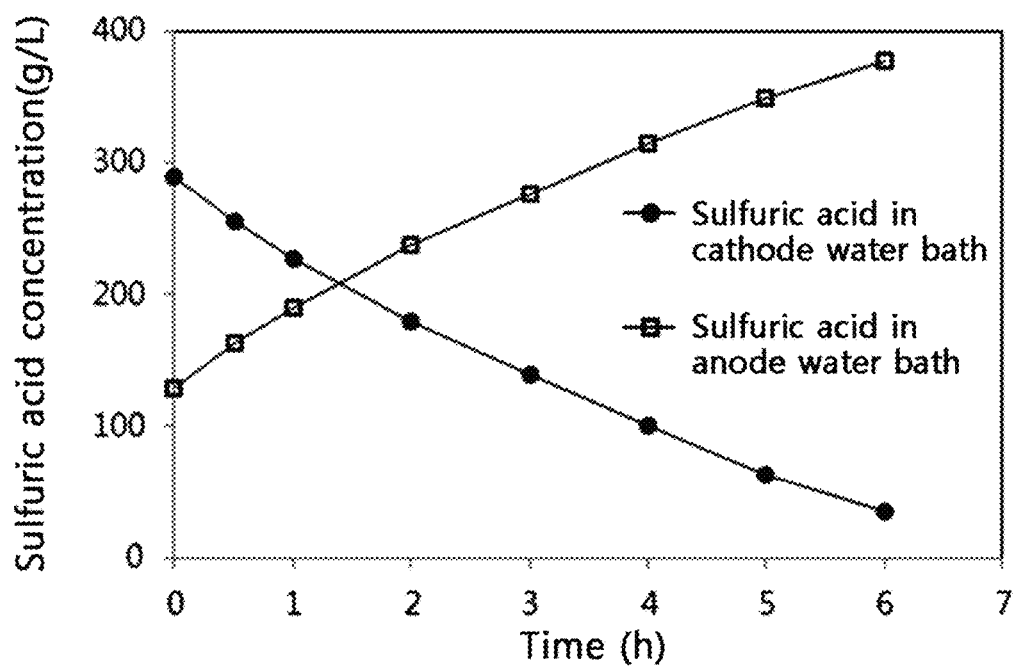

[Fig. 8b]
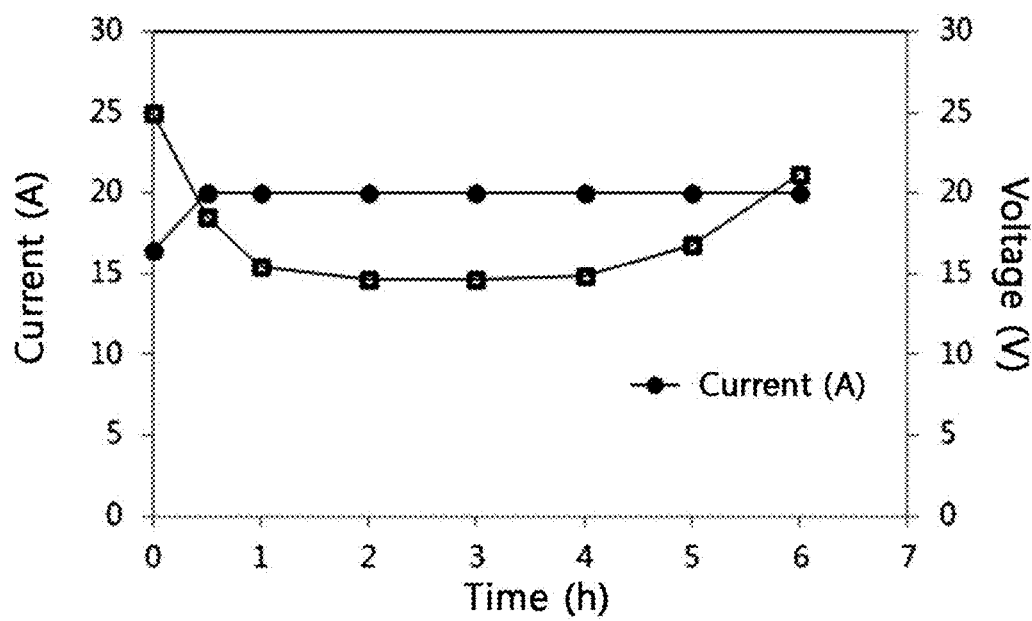
[Fig. 9a]
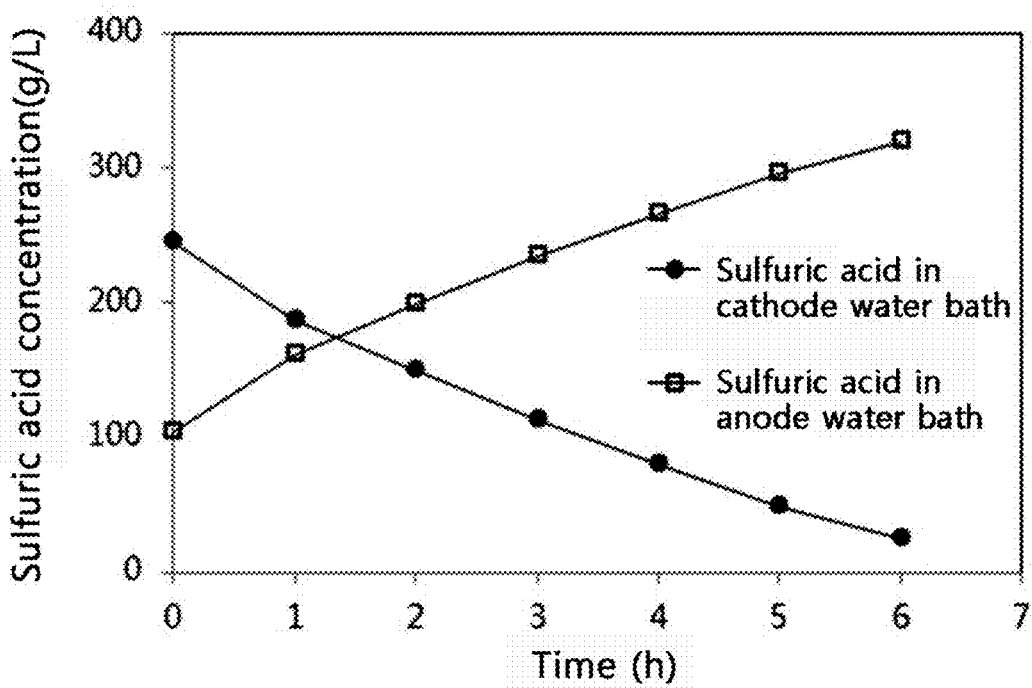

【Fig. 9b】
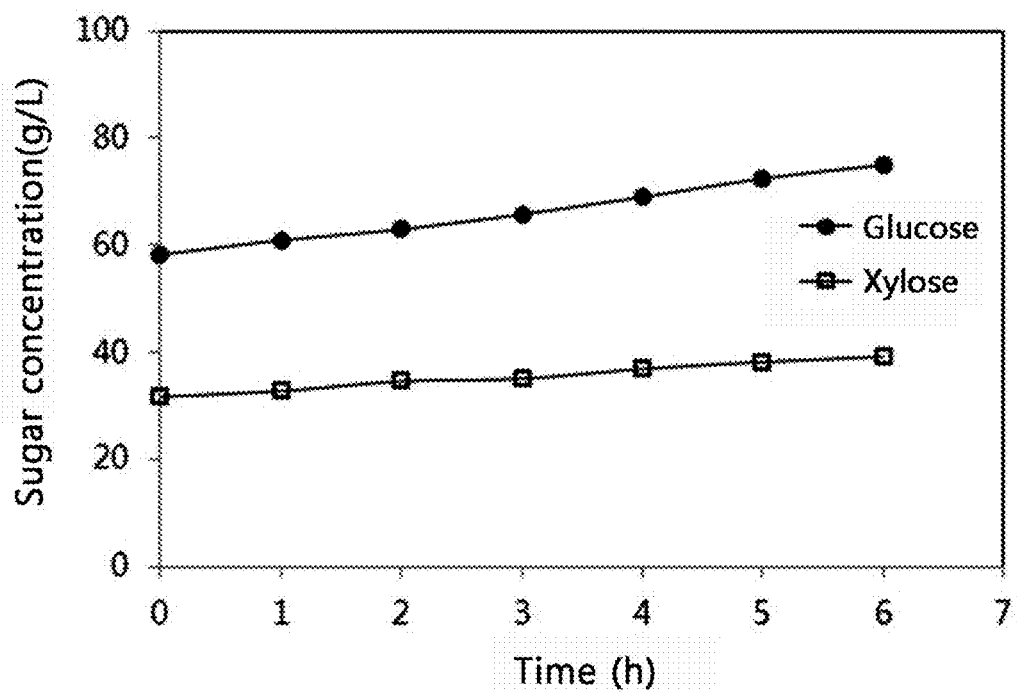
【Fig. 10a】
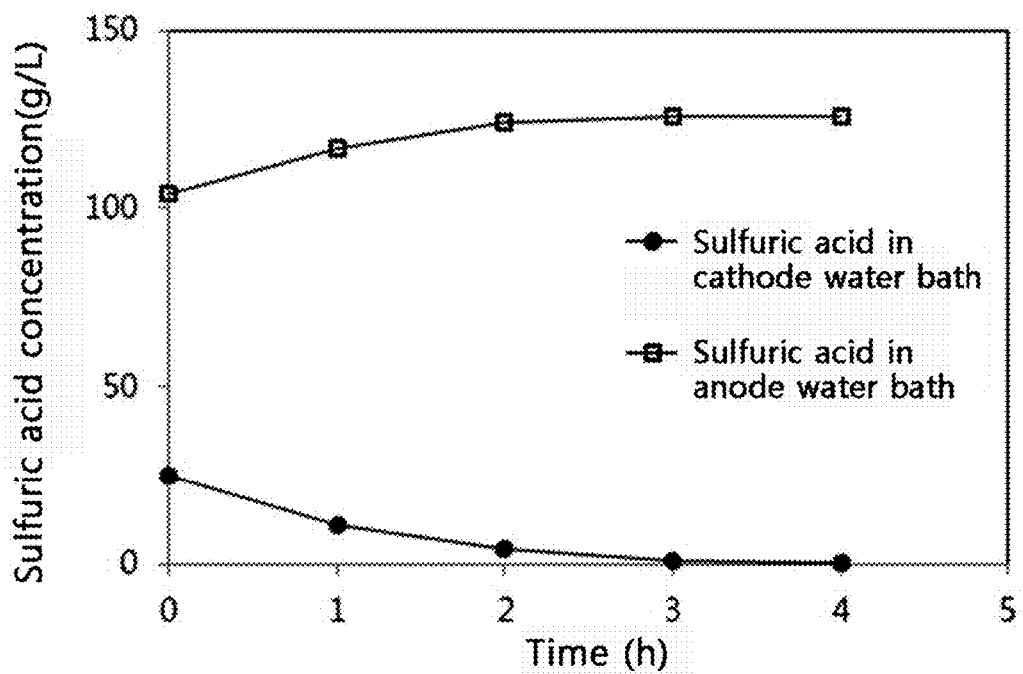

[Fig. 10b]
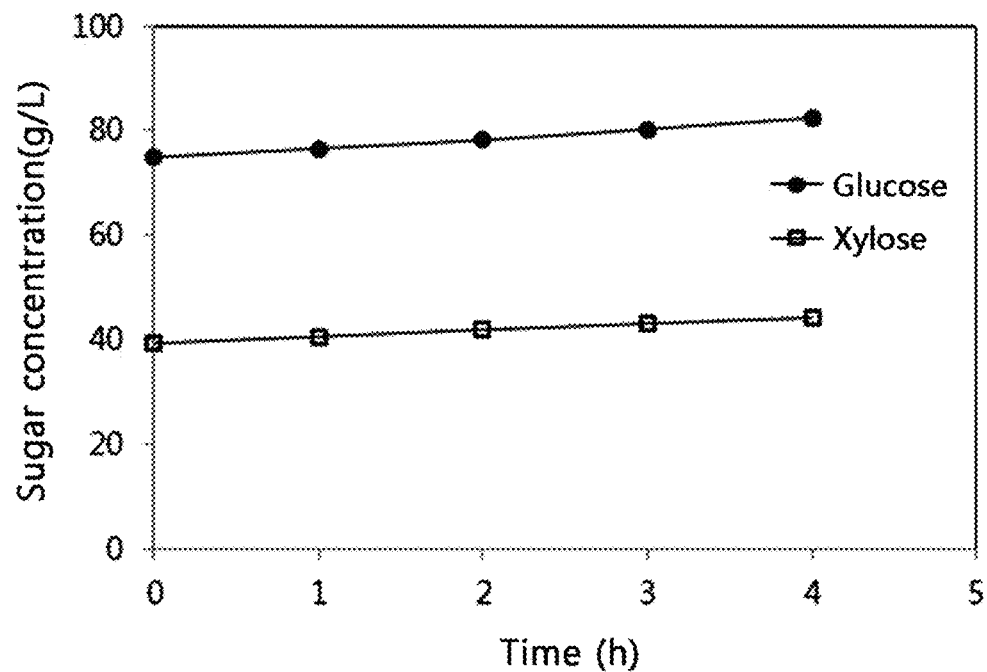
[Fig. 11a]
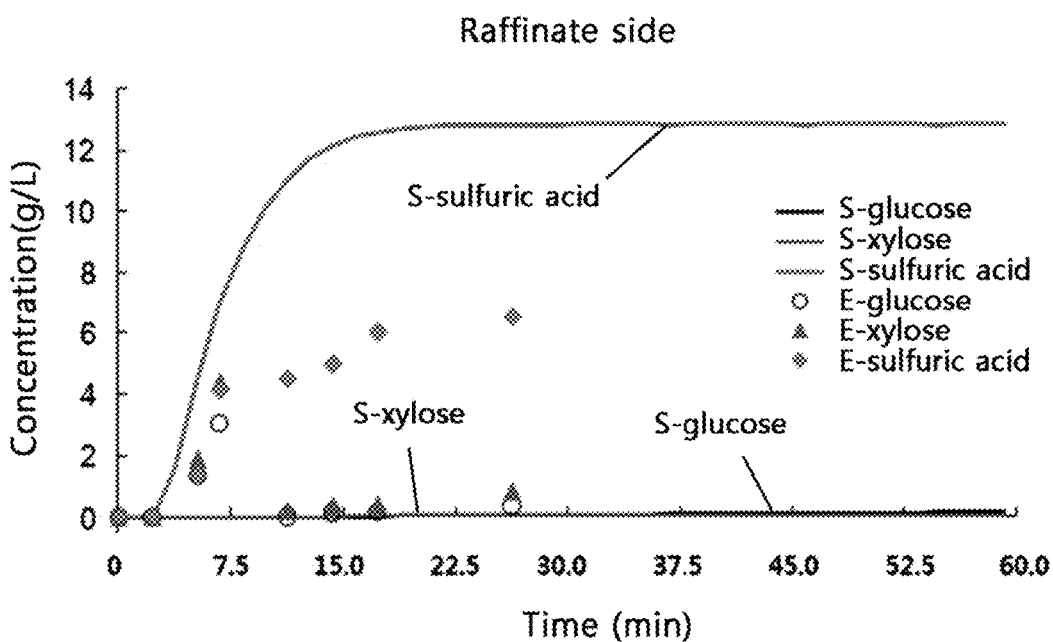

[Fig. 11b]
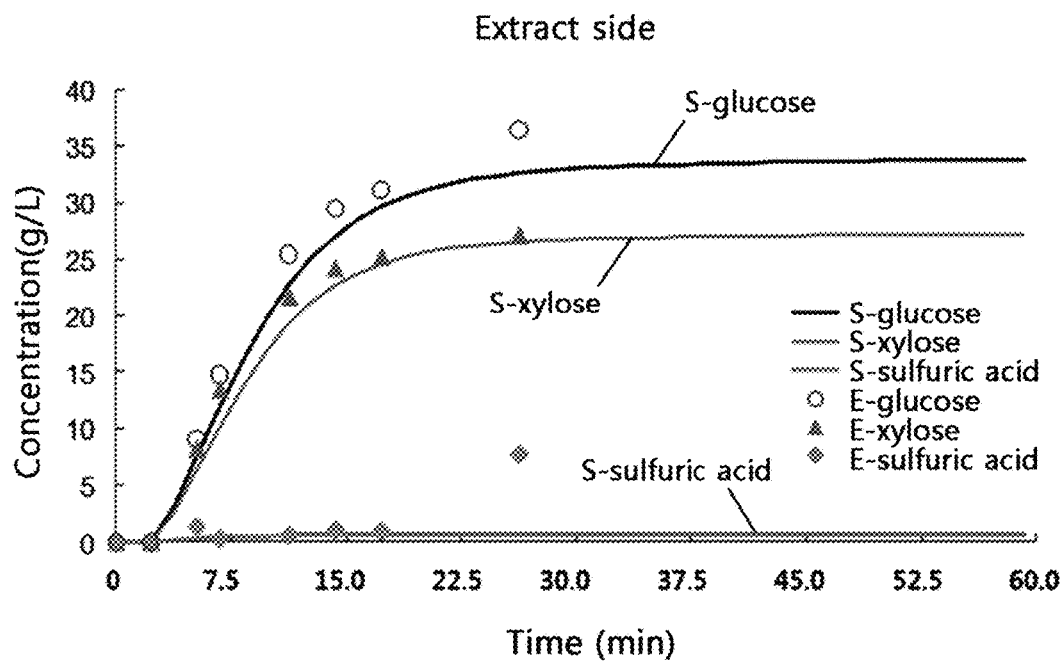
[Fig. 12a]
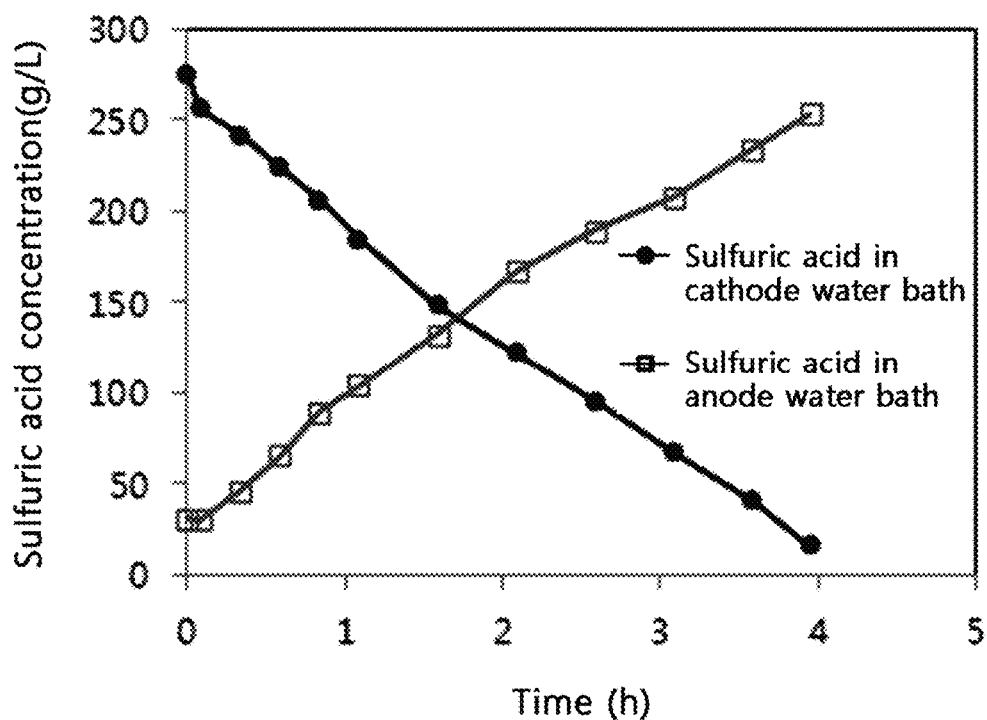

[Fig. 12b]
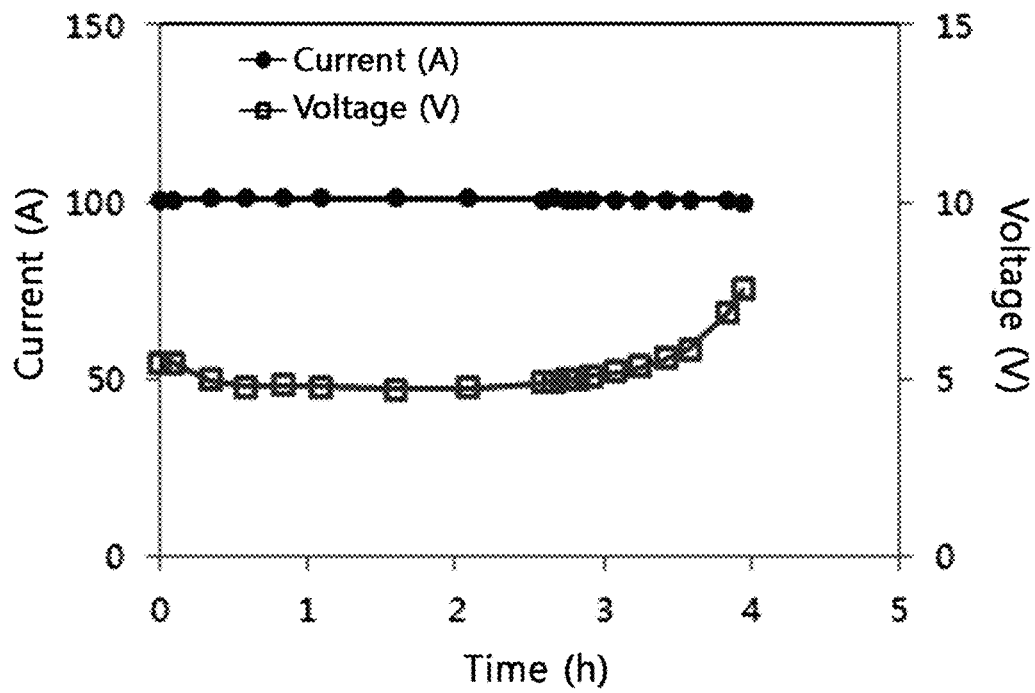
[Fig. 12c]
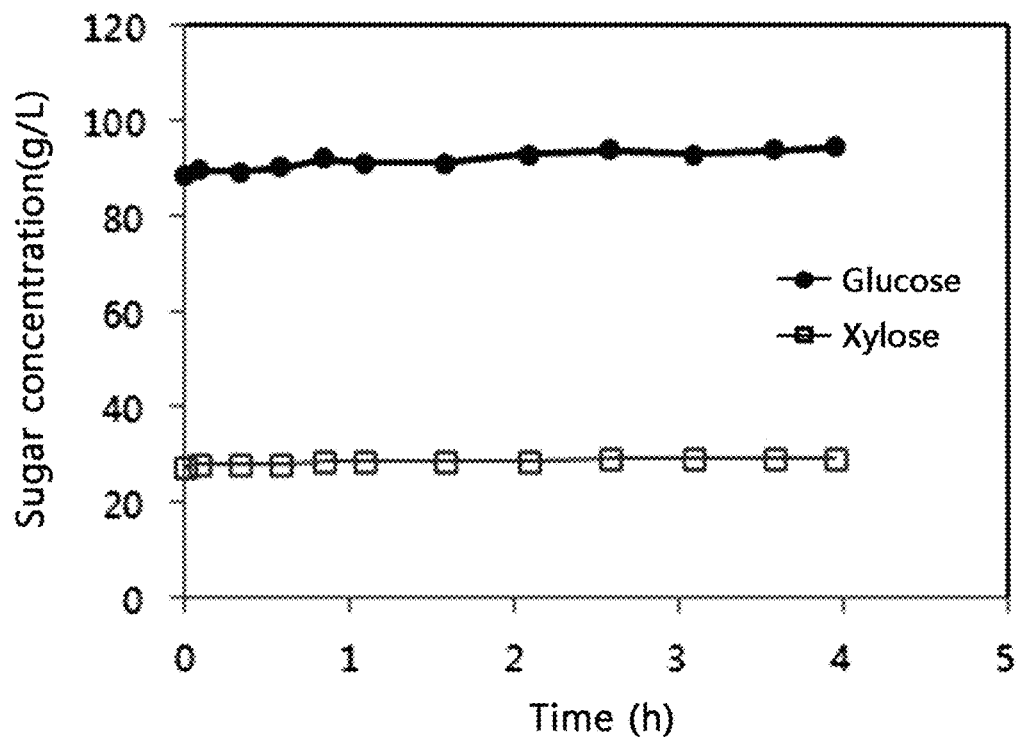

APPARATUS AND METHOD FOR BIOENERGY PRODUCTION USING REGENERATED ACID SOLUTION

CROSS REFERENCE TO RELATED PATENT APPLICATIONS

This application claims the benefit under 35 U.S.C. Section 371, of PCT International Application No. PCT/KR2015/009880, filed Sep. 21, 2015, which claimed priority to Korean Patent Application No. 10-2014-0132605 filed Oct. 1, 2014, the disclosures of which are hereby incorporated by the references.

TECHNICAL FIELD

The present invention relates to an apparatus and method for bioenergy production by which high concentrations of sugars can be obtained in high yield from biomass irrespective of the kind of the biomass and a concentrated acid solution can be recovered for reuse.

BACKGROUND ART

The production and utilization of bioenergy using biomass are becoming increasingly important to cope with petroleum resource depletion and emissions of global warming gases arising from the use of petroleum resources.

Bioenergy as substitute energy for petroleum can be produced by extracting oil components from hydrocarbon-rich plants and seaweeds. As an alternative, bioenergy can be produced by chemically or biologically treating biomass to separate sugar components, which are then converted to the corresponding alcohols through fermentation. Lignocellulosic biomass is a non-edible part of plants and is composed of lignin, cellulose, and hemicellulose. The separated cellulose and hemicellulose can be converted to monosaccharides, including pentose (e.g., arabinose and xylose) and hexose sugars (e.g., glucose), which are readily fermented to the corresponding alcohols by microorganisms. Accordingly, a typical process for producing bioalcohol from biomass consists of pretreatment, hydrolysis (or saccharification), fermentation, and distillation steps. According to the pretreatment step, biomass is finely divided, the biomass tissues containing cellulose, hemicellulose, and lignin, which are tightly bound to one another, are loosened, and the hydrolyzable cellulose and hemicellulose are separated from the biomass tissues at a molecular level. In the hydrolysis step, the cellulose and hemicellulose are converted to sugars. The sugars are converted to the corresponding alcohols in the subsequent fermentation step, and the alcohols are isolated and concentrated in the final distillation step.

Many methods have been proposed for the pretreatment of biomass, for example, by steam explosion, the use of dilute acids, such as dilute sulfuric acid or hydrochloric acid, the use of concentrated acids, such as concentrated sulfuric acid, the use of alkalis, such as sodium hydroxide or ammonia, and the extraction with organic solvents. The steam explosion does not use any harmful chemicals but is limited in extracting cellulose and hemicellulose with steam. Another disadvantage of the steam explosion is that harmful components are produced from the raw material for a prolonged pretreatment time. The use of dilute acids is advantageous in that even hemicellulose can be extracted but requires high pretreatment temperature and pressure conditions and a long operation time, inevitably resulting in the production of considerable amounts of toxic substances, such as furfurals and phenols. The use of concentrated acids enables the extraction of cellulose and hemicellulose within a short time and can thus minimize the production of toxic substances during pretreatment. However, this method incurs a considerable cost in recovering the acids after use and regenerating the acids to high concentrations. By the use of alkalis, lignin is dissolved and cellulose and hemicellulose are caked into a solid mass, which is hydrolyzed in the subsequent step. According to this method, a large amount of liquid alkali waste is generated, lignin is difficult to completely remove from the solid cake as a raw material for hydrolysis, and many problems are encountered in handling the solid cake during processing in an apparatus. The use of organic solvents causes less loss of cellulose and hemicellulose during extraction but incurs a high recovery cost. The organic solvents whose boiling points are low tend to be lost.

Particularly, the use of concentrated acids is advantageous in pretreating various biomasses due to the outstanding ability of concentrated acids to extract polysaccharide structures like cellulose and hemicellulose within a short time and convert the polysaccharide structures to molecular units. In addition, concentrated aqueous acid solutions can also be used for the subsequent saccharification (or hydrolysis) of extracted polysaccharides to make hydrolyzates after pretreatment, achieving the highest hydrolysis yield among methods for producing biomass hydrolyzates. Successful separation of the aqueous acid solutions from the hydrolyzates after use in the pretreatment and hydrolysis steps and sufficient concentration of the aqueous acid solutions enable recycling of the acids. Therefore, the use of concentrated acids would be very useful for biomass pretreatment and subsequent hydrolysis.

A continuous adsorption-separation method based on the use of simulated moving bed (SMB) columns is known in which an acid hydrolyzate (acid-containing hydrolyzate) obtained by pretreatment and hydrolysis with a concentrated aqueous acid solution (concentrated sulfuric acid) are separated into sugars and the acid, which are then recovered. This method uses a system having a construction in which a plurality of chromatography columns for selective adsorption and separation of sugars or sulfuric acid are installed and valves and a pump for continuous sample supply and continuous product discharge are connected to each column. Due to this construction, the system enables continuous separation of sugars and sulfuric acid from the hydrolyzate. However, the separation of sugars and sulfuric acid requires the use of a large amount of water as a carrier, causing dilution of sulfuric acid and sugars to several wt % (hereinafter, the concentrations of sulfuric acid and sugars are expressed as weight percentages (wt %)). For sulfuric acid recycling, the dilute aqueous solution of several % sulfuric acid should be concentrated by distillation. For efficient sugar fermentation, the sugar concentration of the discharged hydrolyzate should also be increased to at least about 10%. However, this concentration involves a high energy cost and is thus inefficient. The SMB system uses chromatography columns packed with expensive adsorbents and its construction is complicated, making the operation very complex. When the acid hydrolyzate has a high acid concentration, the adsorbents undergo severe swelling or shrinkage upon acid adsorption, resulting in low separation efficiency. The repeated adsorption-desorption cycles deteriorate the durability of the adsorbents. For these reasons, the SMB system is not easy to apply to pretreatment and hydrolysis processes using concentrated sulfuric acid.

Thus, there is a need for an economically efficient method by which an acid and sugars are separated from an acid hydrolyzate while minimizing loss of the sugars from the acid hydrolyzate, and at the same time, a concentrated aqueous sulfuric acid solution can be recovered for reuse.

DETAILED DESCRIPTION OF THE INVENTION

Technical Problem

One object of the present invention is to provide an apparatus for bioenergy production by which sugars can be obtained in high yield from biomass irrespective of the kind of the biomass and a concentrated acid solution can be recovered for reuse.

A further object of the present invention is to provide a method for bioenergy production.

Technical Solution

One aspect of the present invention provides an apparatus for bioenergy production using a regenerated acid solution, including: a pretreatment tank where biomass and a first acid solution are stirred to extract cellulose and hemicellulose as sugar components from the biomass; a hydrolysis tank where water is added to the pretreated mixture transferred from the pretreatment tank such that the concentration of the acid is reduced and the sugar components are hydrolyzed to produce an acid hydrolyzate; a first sugar-acid separation tank where the acid hydrolyzate is separated into a second acid solution and a first hydrolyzate; a second sugar-acid separation tank where the first hydrolyzate is separated into a third acid solution and a second hydrolyzate; a fermentation tank where the second hydrolyzate is fermented to produce bioenergy; and an acid solution concentration tank where a mixture of the second acid solution transferred from the first sugar-acid separation tank and the third acid solution transferred from the second sugar-acid separation tank is concentrated to a higher level for reuse.

The apparatus may further include an acid solution return line for returning a fourth acid solution concentrated in the acid solution concentration tank to the pretreatment tank.

The apparatus may further include a solid-liquid separation tank where the acid hydrolyzate and lignin-containing solids produced as a result of the hydrolysis in the hydrolysis tank are separated.

The apparatus may further include a neutralization tank where the second hydrolyzate transferred from the second sugar-acid separation tank is neutralized with an alkaline substance before fermentation.

The third acid solution separated in the second sugar-acid separation tank may be added to the first sugar-acid separation tank.

The first sugar-acid separation tank is an electrolysis tank including a cathode water bath and an anode water bath separated by an anion separator wherein the acid hydrolyzate is added to the cathode water bath and water or an acid solution is added to the anode water bath.

The second sugar-acid separation tank is an electrolysis tank including a cathode water bath and an anode water bath separated by an anion separator wherein the first hydrolyzate is added to the cathode water bath and water or an acid solution is added to the anode water bath.

Each of the anode water baths and the cathode water baths of the first and second sugar-acid separation tanks may include a low-speed agitator to maintain the solution concentration at a constant level with stirring during electrolysis, and each of the anode water baths may include a cooling coil to maintain the solution temperature of the separation tank at a constant level.

The anion separator of the second sugar-acid separation tank may have a size 1 to 8 times larger than that of the anion separator of the first sugar-acid separation tank.

Each of the first and second sugar-acid separation tanks may include an acid solution storage tank to which an acid solution obtained after sugar-acid separation is transferred and a hydrolyzate storage tank to which a hydrolyzate obtained after sugar-acid separation is transferred, the two storage tanks may be provided separately from the electrolysis tank. Each of the first and second sugar-acid separation tanks may include an anode and a cathode, the anode may have a plurality of holes in the lower portion thereof, the cathode may have a plurality of holes in the lower portion thereof, the acid solution may be supplied and discharged through a supply port and a discharge port, respectively, the hydrolyzate may be supplied and discharged through a supply port and a discharge port, respectively, and the supply ports may be opposite to the discharge ports through the perforated anodes and cathodes.

A constant current of 2 to 20 amperes (A) per 15 to 16 cm$^2$ of the anion separator may be maintained in each of the first sugar-acid separation tank and the second sugar-acid separation tank.

The voltage applied to each of the first sugar-acid separation tank and the second sugar-acid separation tank may be maintained at 30 V or less.

The first hydrolyzate may be treated in the second sugar-acid separation tank such that the sugar concentration of the second hydrolyzate is from 70 to 150 g/L.

The first hydrolyzate may be treated in the second sugar-acid separation tank such that the acid concentration of the second hydrolyzate is 1% or less.

The first, second, third, and fourth acid solutions may be aqueous sulfuric acid solutions. Particularly, the first acid solution and the fourth acid solution may be aqueous solutions of 50 to 97% sulfuric acid.

The biomass may be herbal biomass, woody biomass, starchy biomass or seaweed biomass or may be derived from organic waste resources. The hydrolyzed sugars may be selected from the group consisting of glucose, xylose, galactose, fructose, and arabinose.

The alkaline substance may be an aqueous solution of at least one alkali selected from the group consisting of calcium hydroxide ($Ca(OH)_2$), calcium oxide (CaO), calcium carbonate ($CaCO_3$), calcium bicarbonate ($Ca(HCO_3)_2$), sodium hydroxide (NaOH), sodium carbonate ($Na_2CO_3$), sodium bicarbonate ($NaHCO_3$), potassium hydroxide (KOH), potassium carbonate ($K_2CO_3$), and potassium bicarbonate ($KHCO_3$).

Another aspect of the present invention provides a method for bioenergy production using a regenerated acid solution, including: pretreating biomass with a first acid solution to extract sugars from the biomass and hydrolyzing the sugars to prepare an acid hydrolyzate; primarily electrolyzing the acid hydrolyzate into a second acid solution and a first hydrolyzate; secondarily electrolyzing the first hydrolyzate into a third acid solution and a second hydrolyzate; fermenting the second hydrolyzate to produce bioenergy; and distilling a mixture of the second acid solution and the third acid solution to increase the acid concentration of the mixture for reuse.

Each of the primary electrolysis and the secondary electrolysis may be performed in an electrolysis tank including a cathode water bath and an anode water bath separated by an anion separator wherein the acid hydrolyzate or the first hydrolyzate is added to the cathode water bath and water or an acid solution is added to the anode water bath.

The third acid solution separated by the secondary electrolysis may be reused for the primary electrolysis.

Each electrolysis may be performed while maintaining a constant current of 2 to 20 amperes (A) per 15 to 16 $cm^2$ of the anion separator.

The anion separator of the electrolysis tank for the secondary electrolysis may have a size 1 to 8 times larger than that of the anion separator of the electrolysis tank for the primary electrolysis.

The secondary electrolysis may be performed such that the sugar concentration of the second hydrolyzate is from 70 to 150 g/L.

The secondary electrolysis may be performed such that the acid concentration of the second hydrolyzate is 1% or less.

The second acid solution and the first hydrolyzate may be transferred from the first sugar-acid separation tank to an external acid solution stirred tank and an external hydrolyzate stirred tank using pumps during the electrolysis, respectively, the concentrations of the second acid solution and the first hydrolyzate in the stirred tanks may be maintained constant, the temperatures of the second acid solution and the first hydrolyzate in the stirred tanks may be adjusted, and the second acid solution and the first hydrolyzate in the stirred tanks may be recycled to the anode water bath and the cathode water bath of the first sugar-acid separation tank, respectively.

The third acid solution and the second hydrolyzate may be transferred from the second sugar-acid separation tank to an external acid solution stirred tank and an external hydrolyzate stirred tank using pumps during the electrolysis, respectively, the concentrations of the third acid solution and the second hydrolyzate in the stirred tanks may be maintained constant, the temperatures of the third acid solution and the second hydrolyzate in the stirred tanks may be adjusted, and the third acid solution and the second hydrolyzate may be recycled to the anode water bath and the cathode water bath of the second sugar-acid separation tank, respectively.

The acid solution separated and recovered in the anode water bath of the second sugar-acid separation tank may be added to the anode water bath of the first sugar-acid separation tank.

Advantageous Effects

The apparatus of the present invention uses a regenerated acid solution and can produce sugars in high yield from various kinds of biomasses, resulting in the production of a large amount of bioalcohol as bioenergy. An acid solution is diluted for sugar hydrolysis and is concentrated while passing through the sugar-acid separation tanks and the acid solution concentration tank. The concentrated acid solution is recovered from the acid solution concentration tank and is then reused in the pretreatment bath. The use of the regenerated acid solution is advantageous from an economic viewpoint. According to the method of the present invention, primary electrolysis and secondary electrolysis may be performed separately. This is effective in separating the acid solution and efficiently contributes to the reduction of energy consumption.

BRIEF DESCRIPTION OF DRAWINGS

FIG. 1 is a block diagram illustrating a method for producing bioenergy and regenerating an aqueous sulfuric acid solution according to one embodiment of the present invention.

FIG. 2 is a diagram illustrating an open electrolysis tank equipped with a cooling coil and agitators according to one embodiment of the present invention.

FIG. 3a is a closed electrolysis tank including an anode water bath, from which an aqueous sulfuric acid solution is transferred to an external stirred tank and to which the aqueous sulfuric acid solution is returned, and a cathode water bath, from which an acid hydrolyzate is transferred to an external stirred tank and to which the acid hydrolyzate is returned, according to another embodiment of the present invention.

FIG. 3b is an exploded diagram illustrating an anode, a cathode, an anion separator, and an anion separator support of a closed electrolysis tank according to one embodiment of the present invention.

FIG. 3c is a diagram illustrating an anode and a cathode of a closed electrolysis tank according to one embodiment of the present invention.

FIG. 4a shows changes in the concentration of sulfuric acid in an anode water bath and a cathode water bath during electrolysis in Comparative Production Example 1.

FIG. 4b shows changes in voltage and current applied to a cathode and an anode with varying concentrations of sulfuric acid during electrolysis in Comparative Production Example 1.

FIG. 4c shows time-dependent changes in the concentration of sugars in a hydrolyzate in a cathode water bath in Comparative Production Example 1.

FIG. 5a shows changes in the concentration of sulfuric acid in an anode water bath and a cathode water bath during primary electrolysis in Production Example 1.

FIG. 5b shows changes in voltage and current applied to a cathode and an anode with varying concentrations of sulfuric acid during primary electrolysis in Production Example 1.

FIG. 5c shows time-dependent changes in the concentration of sugars in a hydrolyzate in a cathode water bath during primary electrolysis in Production Example 1.

FIG. 6a shows changes in the concentration of sulfuric acid in an anode water bath and a cathode water bath during secondary electrolysis in Production Example 1.

FIG. 6b shows changes in voltage and current applied to a cathode and an anode with varying concentrations of sulfuric acid during secondary electrolysis in Production Example 1.

FIG. 6c shows changes in the concentration of sugars in a hydrolyzate in a cathode water bath with time during secondary electrolysis in Production Example 1.

FIG. 7a shows time-dependent changes in the concentration of sulfuric acid in an anode water bath and a cathode water bath during secondary electrolysis in a closed sugar-acid separation tank using a large-sized anion separator in Production Example 2.

FIG. 7b shows changes in voltage and current applied to a cathode and an anode with varying concentrations of sulfuric acid during secondary electrolysis in a closed sugar-acid separation tank using a large-sized anion separator in Production Example 2.

FIG. 8a shows time-dependent changes in the concentration of sulfuric acid in an anode water bath and a cathode water bath during primary electrolysis in a closed sugar-acid separation tank after an aqueous sulfuric acid solution recovered after secondary electrolysis was added to the anode water bath in Production Example 3.

FIG. 8b shows changes in voltage and current applied to a cathode and an anode with varying concentrations of sulfuric acid during primary electrolysis in a closed sugar-acid separation tank after an aqueous solution of sulfuric acid recovered after secondary electrolysis was added to the anode water bath in Production Example 3.

FIG. 9a shows changes in the concentration of sulfuric acid in an anode water bath and a cathode water bath during primary electrolysis in Example 1.

FIG. 9b shows time-dependent changes in the concentration of sugars in a hydrolyzate in a cathode water bath during primary electrolysis in Example 1.

FIG. 10a shows changes in the concentration of sulfuric acid in an anode water bath and a cathode water bath during secondary electrolysis in Example 1.

FIG. 10b shows time-dependent changes in the concentration of sugars in a hydrolyzate in a cathode water bath during secondary electrolysis in Example 1.

FIG. 11a shows time-dependent changes in the concentration of sulfuric acid, glucose, and xylose at a raffinate side from the beginning of sulfuric acid discharge in Comparative Example 1.

FIG. 11b shows time-dependent changes in the concentration of sulfuric acid, glucose, and xylose at an extract side from the beginning of sugar discharge in Comparative Example 1.

FIG. 12a shows changes in the concentration of sulfuric acid in an anode water bath and a cathode water bath during primary electrolysis in Example 2.

FIG. 12b shows changes in voltage and current applied to a cathode and an anode with varying concentrations of sulfuric acid during primary electrolysis in Example 2.

FIG. 12c shows time-dependent changes in the concentration of sugars in a hydrolyzate in a cathode water bath during primary electrolysis in Example 2.

BEST MODE FOR CARRYING OUT THE INVENTION

The present invention is directed to an apparatus and method for bioenergy production by which sugars can be obtained in high yield from biomass irrespective of the kind of the biomass and a concentrated acid solution can be recovered for reuse.

Specifically, according to the apparatus and method of the present invention, biomass is pretreated with a concentrated acid solution to extract sugars from the biomass, the sugars are hydrolyzed, the acid hydrolyzate is electrolyzed into a hydrolyzate and an acid solution, and the hydrolyzate is fermented to produce bioalcohol as bioenergy. In addition, the acid solution is recovered, concentrated to the same level as the concentrated acid solution used for the pretreatment, and reused for bioenergy production.

The present invention will now be described in detail.

As illustrated in FIG. 1, a bioenergy production apparatus 100 of the present invention includes a pretreatment tank 110, a hydrolysis tank 120, a first sugar-acid separation tank 140, a second sugar-acid separation tank 150, a fermentation tank 170, and an acid solution concentration tank 180. The apparatus 100 may further include a solid-liquid separation tank 130, an acid solution return line a, and a neutralization tank 160.

Pretreatment Tank

In the pretreatment tank 110, biomass and a first concentrated acid solution are stirred to extract sugar components from the biomass.

First, a biomass powder having a water content of 5 to 15 wt % is mixed with an acid solution having an acid concentration of 50 to 97%, preferably 65 to 85%, are mixed in a weight ratio of 1:1-5, preferably 1:1.5-3. The mixture is stirred at 25 to 50° C. for 10 to 15 minutes to extract sugar components from the biomass. The pretreatment with the concentrated acid solution enables uniform extraction of various kinds of sugar components with stirring at a low temperature. If the biomass powder is mixed with the acid solution in a weight ratio outside the range defined above, only particular sugar components can be extracted and other sugar components may not be extracted or the biomass may be degraded into very toxic substances.

The biomass may be herbal biomass, woody biomass, starchy biomass or seaweed biomass or may be derived from organic waste resources. Examples of the organic waste resources include waste wood, farm and forest byproducts, and food byproducts.

Hydrolysis Tank and Solid-liquid Separation Tank

The mixture obtained after pretreatment in the pretreatment tank 110 is in the form of a slurry. The pretreated mixture is hydrolyzed in the hydrolysis tank 120 to produce an acid hydrolyzate.

Specifically, the slurry is diluted with water until the acid concentration reaches 10 to 40%, preferably 25 to 35%. For hydrolysis, the dilution is stirred at 60 to 90° C., preferably 70 to 80° C., for 50 to 70 minutes. When a brown liquid is separated from solids during the hydrolysis, the reaction is stopped.

In the solid-liquid separation tank 130, the hydrolysis mixture is subjected to liquid-solid separation. The liquid is the acid hydrolyzate containing the acid solution. The liquid is transferred to the first sugar-acid separation tank 140 for the subsequent processing. The solids are lignin-containing solids and are discharged to the outside through a solid discharge line c.

The hydrolyzed sugars may be selected from the group consisting of glucose, xylose, galactose, fructose, and arabinose.

First Sugar-acid Separation Tank

The first sugar-acid separation tank is exemplified in FIG. 2. As illustrated in FIG. 2, the first sugar-acid separation tank includes a cathode water bath 142, an anode water bath 141, and an anion separator 145 separating the cathode water bath and the anode water bath. The first sugar-acid separation tank 140 may be an open electrolysis tank in which a low-speed agitator is installed in each of the water baths and a cooling coil is installed in the anode water bath 141.

FIG. 3a illustrates another example of the first sugar-acid separation tank. As illustrated in FIG. 3a, the first sugar-acid separation tank includes a cathode water bath 242, an anode water bath 241, and an anion separator 247 separating the cathode water bath and the anode water bath. The first sugar-acid separation tank may be a closed electrolysis tank 240 in which the anode water bath 241 is connected to an external acid solution storage tank 249 and the cathode water bath 242 is connected to an external hydrolyzate storage tank 256.

[Open Electrolysis Tank]

The acid hydrolyzate is added to the cathode water bath 142 of the electrolysis tank 140 and water or an acid solution is added to the anode water bath 141. In the electrolysis tank, electrolysis is performed for 3 to 10 hours, preferably for 3 to 6 hours. During the electrolysis, the acid of the acid hydrolyzate moves from the cathode water bath 142 to the anode water bath 141. As a result, the acid is not substantially present and the sugars remain concentrated in the cathode water bath 142. Salt anions migrate from the cathode water bath 142 to the anode water bath 141 during the electrolysis, and as a result, hydrogen gas and oxygen gas are generated in the cathode water bath 142 and the anode water bath, respectively.

The current applied to the electrolysis tank is from 2 to 20 A per 15 to 16 cm² of the anion separator, which corresponds to a current density of 0.125 to 1.25 A/cm² per unit area of the anion separator. Within this range, the anion separator can withstand the flux of salt anions per unit time. The voltage applied to the electrolysis tank is limited to 30 V or less while maintaining the current density as high as possible. This is advantageous in promoting the migration of salt anions.

Considering the relationship between the current and the electrode area, the current density per unit area of the electrode is maintained at 0.1 to 1.0 A/cm², which is more advantageous in promoting the migration of salt anions.

The voltage applied to the open electrolysis tank 140 is maintained at 30 V or less, preferably 3 to 10V. At this time, the distance between a cathode and an anode opposite to each other through the anion separator is adjusted to the range of 4 to 30 mm. Within this range, the normal operating voltage can be reduced to 5 V or less, preferably 3 to 5 V.

If the voltage is lower than the lower limit defined above, the migration velocity of salt ions is low, delaying the separation of the sugars and the acid. Meanwhile, if the voltage is higher than the upper limit defined above, the migration velocity of salt ions passing through the anion separator is high but rapid damage to the anion separator is caused. In this case, electrical resistances in the anode and the cathode may increase, resulting in high electrode temperatures. The high electrode temperatures cause high energy loss. The organic matter may be carbonized on the cathode surface, impeding continuous electrolysis.

The anion separator 145 allows the migration of salt anions from the cathode water bath to the anode water bath therethrough. The anion separator blocks the migration of hydrogen ions ($H^+$). Hydrogen ions ($H^+$) are reduced to hydrogen gas ($H_2$) at the cathode of the cathode water bath and hydroxyl ions ($OH^-$) are oxidized to oxygen gas ($O_2$) at the anode of the anode water bath.

The anode 143 of the anode water bath 141 and the cathode 144 of the cathode water bath 142 may be each independently selected from: metal electrodes; noble metal electrodes; carbon electrodes; and DSA type electrodes obtained by coating a titanium (Ti) or tantalum (Ta) metal plate with a metal oxide, such as iridium oxide ($IrO_2$), ruthenium oxide ($RuO_2$) or tantalum oxide ($Ta_2O_5$). The anode, where oxidation occurs, tends to electrically corrode. It is thus preferred that the anode is a platinum electrode, an amorphous carbon electrode or a DSA type electrode, where slow electrical corrosion occurs. The cathode, where reduction occurs, is electrically protected. Accordingly, the cathode may be any general metal electrode, such as a carbon steel electrode. The cathode is preferably a platinum electrode, a platinum-plated metal electrode, an amorphous carbon electrode, a crystalline carbon electrode or a DSA type electrode rather than a carbon steel electrode because sulfuric acid accommodated in the cathode water bath causes chemical corrosion of the electrode. The use of a crystalline carbon electrode as the anode is not suitable because the carbon electrode tends to peel in a concentrated acid solution, particularly an aqueous sulfuric acid solution, causing contamination of the solution during long-term use. The use of an amorphous carbon electrode that releases a large amount of heat due to its high inherent electrical resistance is disadvantageous in terms of energy efficiency. Therefore, the two electrodes are preferably platinum electrodes or DSA type electrodes that are stable against electrical and chemical corrosion and have high electrical conductivities.

The first sugar-acid separation tank has a body made of at least one material selected from the group consisting of annealed glass resistant to acid corrosion, glass-lined carbon steel, acid resistant resins, such as polyethylene (PE), polypropylene (PP), and polyvinyl chloride (PVC), fluorinated resins, such as polytetrafluoroethylene (PTFE), polyvinyl fluoride (PVF), and polyvinylidene fluoride (PVDF), fluorinated copolymer resins, such as perfluoroalkoxy (PFA) and fluorinated ethylene propylene (FEP), and fiber-reinforced plastics (FRP). The agitator shafts and impellers may be coated with PTFE or a fluorinated copolymer resin. The cooling coil may be an annealed glass tube coil or a fluorinated resin tube.

Below is a description concerning the separation of a sulfuric acid hydrolyzate into a hydrolyzate and a sulfuric acid solution by electrolysis in the first sugar-acid separation tank 140.

The sulfuric acid of the sulfuric acid hydrolyzate filled in the cathode water bath is ionized into hydrogen ions ($H^+$) and sulfate ions ($HSO_4^-$, $SO_4^{2-}$). When electricity is supplied to the cathode water bath, the hydrogen ions ($H^+$) receive electrons on the surface of the cathode 144 to generate hydrogen ($H_2$) gas and the sulfate ions ($HSO_4^-$, $SO_4^{2-}$) migrate to the anode water bath 141 through the anion separator 145. Hydroxyl ions ($OH^-$) are degraded on the surface of the anode 143 of the anode water bath 141 and lose electrons at the anode side to generate oxygen ($O_2$) gas. Hydrogen ions ($H^+$) created by the dissociation of water and the electrolysis of hydroxyl ions ($OH^-$) meet the sulfate ions ($HSO_4^-$, $SO_4^{2-}$) migrating from the cathode water bath 142 and convert the sulfate ions to sulfuric acid. For example, simultaneously with the electrolysis of water in the anode water bath 141, sulfate ions ($HSO_4^-$, $SO_4^{2}$) migrate from the cathode water bath 142 to the anode water bath 141 to increase the concentration of sulfuric acid in the anode water bath 141.

In summary, the sulfuric acid present in the acid hydrolyzate of the cathode water bath 142 moves to the anode water bath 141, the hydrolyzate, from which the sulfuric acid has been removed, is concentrated in the cathode water bath 142, and the sulfuric acid is concentrated in the anode water bath 141. The increased concentration of the sulfuric acid in the aqueous solution leads to an increase in the temperature of the anode water bath 141 due to the heat of dissolution of the sulfuric acid. The cooling coil 147 installed in the anode water bath 141 prevents the temperature of the anode water bath 141 from rising excessively and serves to maintain the temperature of the aqueous solution in the anode water bath 141 at 50 to 70° C. Each of the agitators 146 installed in the anode water bath 141 and the cathode water bath 142 ensures better mass transfer through the anion separator 145 while maintaining the concentration of the solution constant.

When the sulfuric acid concentration of the cathode water bath 142 is lowered below a predetermined level, PTFE-lined solenoid valves provided under the anode water bath 141 and the cathode water bath 142 are opened to discharge the materials from both water baths. The solenoid valves of the open electrolysis tank 140 may be opened in a specific situation, for example, when the sulfuric acid concentration is lowered to a predetermined level, which is measured using a gauge mounted in the cathode water bath 142, when the aqueous sulfuric acid solution increases above a predetermined level, which is measured using a level gauge mounted in the anode water bath 141, or after the passage of a predetermined electrolysis time, which is previously determined through experimentation. All portions of the aqueous sulfuric acid solution (second acid solution) in the anode water bath 141 of the open first sugar-acid separation tank 140 are transferred to the acid solution concentration tank 180. Alternatively, some portions of the aqueous sulfuric acid solution may be transferred to the acid solution concentration tank 180 and the remaining portions may be transferred to the anode water bath of the second sugar-acid separation tank 150. The hydrolyzate of the cathode water bath 142 is transferred to the second sugar-acid separation tank 150.

[Closed Electrolysis Tank]

The current and voltage applied to the closed electrolysis tank 240, the electrolysis process in the closed electrolysis tank 240, the material for the closed electrolysis tank 240, and the kinds of electrodes of the closed electrolysis tank 240 are the same as those described for the open electrolysis tank 140 and an explanation thereof is thus omitted.

The closed electrolysis tank 240 includes a cathode water bath 242, an anode water bath 241, and an anion separator 247 separating the cathode water bath and the anode water bath. The anode water bath 241 is connected to an external acid solution storage tank 249 and the cathode water bath 242 is connected to an external hydrolyzate storage tank 256. The acid solution of the acid solution storage tank 249 is supplied to the rear side of the anode 243 using a metering pump 248 and the hydrolyzate of the hydrolyzate storage tank 256 is supplied to the rear side of the cathode 245 of the cathode water bath 242 via a filter unit 262 using a metering pump 255. A polypropylene (PP) woven filter is mounted in the filter unit 262 and serves to filter off small amounts of particles remaining in the hydrolyzate. Periodical separation and washing of the filter increases the service life of the anion separator 247.

As illustrated in FIG. 3*b*, each of the anode 243 and the cathode 245 has a plurality of holes in the lower portion thereof. The acid solution and the hydrolyzate pass through the holes and move to the front sides of the anode 243 and the cathode 245, i.e. toward the anion separator 247, respectively. The acid solution and the hydrolyzate move upward at the front sides of the anode 243 and the cathode 245, respectively, and are discharged to the outside. At this time, the acid solution and the hydrolyzate rapidly wash oxygen gas and hydrogen gas generated from the surfaces of the anode 243 and the cathode 245, respectively, move the gases upward, and are discharged to the outside together with the gases. This is effective in lowering the electrical resistances on the surfaces of the anode and the cathode. After cooling in the external tanks, the acid solution and the hydrolyzate are supplied to the rear sides of the anode 243 and the cathode 245, respectively. The acid solution and the hydrolyzate flow downward and move to the front sides of the anode and the cathode, respectively. Thereafter, the acid solution and the hydrolyzate flow upward at the front sides of the anode and the cathode, respectively, and are discharged to the outside. The rear-to-front flows of the acid solution and the hydrolyzate increases the contact time of the acid solution and the hydrolyzate with the anode and the cathode, respectively. The increased contact time is effective in preventing the temperatures of the anode and the cathode from rising.

The shape of the closed electrolysis tank 240 is not particularly limited. For example, the closed electrolysis tank 240 may be in the shape of a square pillar (FIG. 3*a*) or cylinder (FIG. 3*b*). The shape of each of the anode 243 and the cathode 245 is not particularly limited so long as the electrode has a plurality of holes in the lower portion thereof. Preferably, the anode 243 and the cathode 245 have the same shape as the cross-section of the closed electrolysis tank 240.

The migration of salt ions to the anode water bath by electrolysis increases the sulfuric acid concentration of the acid solution. The acid solution is transferred to the acid solution storage tank 249 through a discharge port formed on the anode water bath 241. The hydrolyzate having a reduced sulfuric acid concentration is transferred to the hydrolyzate storage tank 256 through a discharge port formed on the cathode water bath 242. Oxygen gas generated in the anode water bath 241, together with the acid solution, is discharged through the discharge port formed on the anode water bath and hydrogen gas generated in the cathode water bath 242, together with the hydrolyzate, is discharged through the discharge port formed on the cathode water bath.

The acid solution and the hydrolyzate are continuously supplied to and discharged from the anode water bath 241 and the cathode water bath 242, respectively. The continuous supply and discharge induces natural stirring of the solutions in the water baths. The simultaneous discharge of the liquids and the gases always maintains the surfaces of the anode, the cathode, and the anion separator clean. Agitators 251 and 258, thermocouple sheaths 252 and 259, and cooling jackets 250 and 257 are installed in the acid solution storage tank 249 and the hydrolyzate storage tank 256, respectively. Due to this construction, when each solution is stirred, the concentration of the solution is made constant and the temperature of the solution is adjusted to a constant range. Heat exchangers may be further installed in the transfer line through which the acid solution is transferred from the anode water bath 241 to the acid solution storage tank 249 and the transfer line through which the hydrolyzate is transferred from the cathode water bath 242 to the hydrolyzate storage tank 256. As a result of the heat exchange, each solution is rapidly cooled and its temperature is maintained constant.

Oxygen gas is discharged through a nozzle 253 formed on the acid solution storage tank 249 and hydrogen gas is discharged through a nozzle 260 formed on the hydrolyzate storage tank 256. As the electrolysis proceeds, concentrated sulfuric acid is collected in the acid solution storage tank 249 and the hydrolyzate having a reduced sulfuric acid concentration is concentrated and collected in the hydrolyzate storage tank 256. When the concentration or level of the solution in each storage tank reaches a predetermined value, the sugar-acid separation is stopped and the solution is discharged through a solenoid valve provided under the storage tank.

The closed electrolysis tank 240 has no internal agitator and the anode water bath and the cathode water bath are not filled with the acid solution and the acid hydrolyzate all at once, respectively. This can render the sugar-acid separator small and compact. In addition, the closed electrolysis tank 240 was confirmed to achieve similar sugar-acid separation efficiency to that of the open electrolysis tank 140 of FIG. 2 in which internal agitators are installed.

Second Sugar-acid Separation Tank

The structure of the second sugar-acid separation tank 150 is the same as or similar to that of the open electrolysis tank 140 or the closed electrolysis tank 240. The term "similar to" means that the second sugar-acid separation tank 150 includes a cathode water bath, an anode water bath, and an anion separator separating the water baths, like the first sugar-acid separation tank, but the sizes of the water baths and the anion separator may be different from those of the first sugar-acid separation tank.

In the present invention, the first and second sugar-acid separation tanks may be open electrolysis tanks or closed electrolysis tanks. Alternatively, the first sugar-acid separation tank may be an open electrolysis tank and the second sugar-acid separation tank may be a closed electrolysis tank, or vice versa.

Electrolysis is performed in the second sugar-acid separation tank 150 in the same manner as in the first sugar-acid separation tank, except that the first hydrolyzate separated in the first sugar-acid separation tank is added to the cathode water bath instead of the acid hydrolyzate. Electrolysis is performed in the second sugar-acid separation tank 150 until the sulfuric acid concentration of the first hydrolyzate added to the cathode water bath reaches 1% or less. Accordingly, a high voltage is applied to the second sugar-acid separation tank compared to the first sugar-acid separation tank because of the reduced sulfuric acid concentration (i.e. electrolyte concentration) of the cathode water bath. Thus, there is a need to reduce an increase in the voltage applied to the second sugar-acid separation tank as much as possible. This need is preferably met by using the larger anion separator of the second sugar-acid separation tank 150 than that of the first sugar-acid separation tank. If the cathode water bath of the first sugar-acid separation tank has the same size as that of the second sugar-acid separation tank, the second sugar-acid separation tank 150 is provided in plurality. In this case, the second sugar-acid separation tanks 150 may be arranged in parallel. With this arrangement, the moles of sulfate ions ($HSO_4^-$, $SO_4^{2-}$) passing through unit area of each anion separator can be reduced. Specifically, the anion separator of the second sugar-acid separation tank 150 has a size 1 to 8 times, preferably 3 to 5 times, larger than that of the anion separator of the first sugar-acid separation tank 140. The distance between the cathode and the anode opposite to each other through the anion separator is adjusted to the range of 4 to 30 mm. Within this range, the normal operating voltage can be reduced to 5 V or less, preferably 3 to 5 V.

In the second sugar-acid separation tank 150, the temperatures of the anode and the aqueous sulfuric acid solution increase because of the heat of dissolution of the sulfuric acid concentrated in the anode water bath and the high voltage operation. Further, as the sugar concentration of the hydrolyzate in the cathode water bath increases, the viscosity of the hydrolyzate increases and the flowability of the hydrolyzate decreases, resulting in sugar carbonization on the cathode surface in the cathode water bath. Stirring and cooling of the aqueous sulfuric acid solution and the hydrolyzate are of great importance in order to prevent the temperature rise of the anode water bath and the sugar carbonization on the cathode surface. To prevent the carbonization of sugars, the second sugar-acid separation tank is preferably operated in a state in which the sugar concentration of the cathode water bath is diluted to a level required in the fermentation tank. For example, the amount of water is adjusted before electrolysis such that the sugar concentration of the cathode water bath is maintained in the range of 70 to 150 g/L, preferably 90 to 120 g/L. If the sugar concentration is lower than the lower limit defined above, bioenergy is produced at a low rate during subsequent fermentation. Meanwhile, if the sugar concentration exceeds the upper limit defined above, the flowability of the hydrolyzate decreases and the sugars are carbonized on the electrode surface, resulting in an increase in the resistance of the electrode. The increased resistance leads to a considerable separation energy loss. The loss of the sugars by carbonization may deteriorate the production yield of bioenergy.

When the concentration of the sulfuric acid remaining in the hydrolyzate in the cathode water bath of the second sugar-acid separation tank 150 is lowered to 1% or less, the solenoid valves connected to the discharge lines of the anode water bath and the cathode water bath are opened to discharge the materials from the respective baths.

A portion of the aqueous sulfuric acid solution (third acid solution) discharged from the anode water bath of the second sugar-acid separation tank 150 may be transferred to the acid solution concentration tank 180 and a portion thereof may be transferred to the anode water bath of the first sugar-acid separation tank 140. The hydrolyzate present in the cathode water bath of the second sugar-acid separation tank 150 is transferred to the neutralization tank 160.

The material for the second sugar-acid separation tank is the same as that described for the first sugar-acid separation tank.

In the case where only one of the first sugar-acid separation tank and the second sugar-acid separation tank 150 is used, the separation efficiency is lowered, and as a result, a large amount of the acid solution present in the hydrolyzate after separation based on the same sugar-acid separation time, requiring an increased amount of an alkaline solution to neutralize the hydrolyzate. Further, a long time is required for sugar-acid separation after the sulfuric acid concentration of the cathode water bath is reduced to a predetermined level, leading to high energy consumption. Further, a larger amount of the sugars is carbonized, deteriorating the yield of bioenergy.

Acid Solution Concentration Tank

The second acid solution discharged from the first sugar-acid separation tank and the third acid solution discharged from the second sugar-acid separation tank 150 are collected in the acid solution concentration tank 180. Each of the second and third acid solutions has an acid concentration of 10 to 35%. Thereafter, the acid solutions are concentrated using an evaporator such that the concentrated solution (fourth acid solution) has an acid concentration in the range of 50 to 97%, preferably 65 to 85%. Within this range, the concentrated solution can be directly used in the pretreatment tank 110. The high acid concentrations of the collected acid solutions facilitate the preparation of the fourth acid solution without the need to use much energy and time.

The fourth acid solution concentrated in the acid solution concentration tank 180 can be sent to the pretreatment tank 110 through the return line a and can be reused for biomass pretreatment. When an insufficient amount of the fourth acid solution is sent to the pretreatment tank 110, the first acid solution may be supplied to the pretreatment tank 110 through a line b.

The acid solution concentration tank includes a heat exchanger and an evaporator made of acid-resistant annealed glass or glass-lined carbon steel. A two- or multi-stage evaporator is used for high energy efficiency. Alternatively, the acid solution concentration tank may be a distillation tower including a distillation column made of acid-resistant annealed glass or glass-lined carbon steel, a condenser (heat exchanger), and a reboiler made of annealed glass or silicon carbide. The water is removed and the acid solutions are concentrated by distillation in the distillation tower at ambient pressure or reduced pressure.

Neutralization Tank

In the neutralization tank 160, the second hydrolyzate discharged from the second sugar-acid separation tank 150 is neutralized with an aqueous solution of at least one alkali selected from the group consisting of calcium hydroxide ($Ca(OH)_2$), calcium oxide (CaO), calcium carbonate ($CaCO_3$), calcium bicarbonate ($Ca(HCO_3)_2$), sodium hydroxide (NaOH), sodium carbonate ($Na_2CO_3$), sodium bicarbonate ($NaHCO_3$), potassium hydroxide (KOH), potassium carbonate ($K_2CO_3$), and potassium bicarbonate ($KHCO_3$). The neutralization tank 160 serves to remove a small amount of the third acid solution remaining in the second hydrolyzate. The neutralization makes the second hydrolyzate suitable for the subsequent enzymatic reaction.

The neutralized second hydrolyzate is transferred to the fermentation tank 170.

Fermentation Tank

In the fermentation tank 170, the neutralized second hydrolyzate is converted to bioalcohol as bioenergy by enzymatic fermentation. When the conversion to bioenergy approaches about 40%, the fermentation is stopped to avoid possible side reactions and bioenergy is collected.

The first to fourth acid solutions may be selected from the group consisting of sulfuric acid, sulfamic acid, citric acid, succinic acid, maleic acid, and phthalic acid solutions, but are preferably sulfuric acid solutions. Particularly, the first and fourth acid solutions are aqueous solutions of 65 to 85% sulfuric acid and the second and third acid solutions are aqueous solutions of 10 to 35% sulfuric acid.

The present invention also provides a method for bioenergy production using a regenerated acid solution.

Specifically, the method includes: pretreating biomass with a first acid solution to extract polysaccharide structures from the biomass and hydrolyzing the sugar components to prepare an acid hydrolyzate; primarily electrolyzing the acid hydrolyzate into a second acid solution and a first hydrolyzate; secondarily electrolyzing the first hydrolyzate into a third acid solution and a second hydrolyzate; fermenting the second hydrolyzate to produce bioenergy; and distilling a mixture of the second acid solution and the third acid solution to increase the acid concentration of the mixture for reuse.

Each of the primary and secondary electrolysis may be performed in an electrolysis tank including a cathode water bath and an anode water bath separated by an anion separator wherein the acid hydrolyzate is added to the cathode water bath and water or an acid solution is added to the anode water bath.

Each electrolysis may be performed while maintaining a constant current of 2 to 20 amperes (A) per 15 to 16 $cm^2$ of the anion separator and maintaining the voltage applied to the electrolysis tank at 30 V or less.

The secondary electrolysis may be performed such that the sugar concentration of the second hydrolyzate is from 70 to 150 g/L and the acid concentration of the second hydrolyzate is 1% or less.

The following examples are provided to assist in further understanding of the invention. However, these examples are intended for illustrative purposes only. It will be evident to those skilled in the art that various modifications and changes can be made without departing from the scope and spirit of the invention and such modifications and changes are encompassed within the scope of the appended claims.

COMPARATIVE PRODUCTION EXAMPLE 1

Primary Electrolysis (in Open Electrolysis Tank)

30% sulfuric acid, 60 g/L glucose, and 20 g/L xylose were mixed and slowly stirred at 60° C. for 1 h to prepare a hydrolyzate.

500 mL of the hydrolyzate and 500 mL of an aqueous solution of 10% sulfuric acid were added to a cathode water bath and an anode water bath of a first sugar-acid separation tank (open electrolysis tank), respectively. The cathode water bath and the anode water bath of the first sugar-acid separation tank (open electrolysis tank) were separated by an anion separator (diameter of circular liquid contact side: 45 mm, NEOSEPTA-AMX anion-exchange membrane, ASTOMS). Platinum electrodes having the same size (5 cm×8 cm) were immersed in the aqueous solutions in the water baths. Electrolysis was performed by opening a rated voltage to a maximum of 30 V in a DC rectifier and allowing a fixed current of 20 A to flow between both electrodes in a constant current mode.

The electrolysis was performed without using agitators in the anode and cathode water baths.

Changes in the concentration of sulfuric acid, glucose, and xylose in the anode and cathode water baths were analyzed using a liquid chromatograph (Agilent model 1200) with an Aminex HPX-87H column (7.8 mmD×300 mmL) and a refractive index detector.

TEST EXAMPLE 1

Measurement of Changes in Concentration of Sugars and Sulfuric Acid During Electrolysis in Comparative Production Example 1

FIG. 4a shows changes in the concentration of sulfuric acid in the anode water bath and the cathode water bath during electrolysis in Comparative Production Example 1. FIG. 4b shows changes in voltage and current applied to the cathode and the anode with varying concentrations of sulfuric acid during electrolysis in Comparative Production Example 1. FIG. 4c shows time-dependent changes in the concentration of sugars in the hydrolyzate in the cathode water bath in Comparative Production Example 1.

As shown in FIGS. 4a to 4c, the concentration of sulfuric acid in the cathode water bath was 25.5% (285 g/L) at the initial stage of electrolysis but was reduced to 7.2% at 5 h after electrolysis, 3% at 6 h after electrolysis, and 1% at 7 h after electrolysis. These results confirm that the sulfuric acid concentration of the hydrolyzate decreased in proportion to the electrolysis time until it reached 3%, and thereafter, its reduction rate decreased gradually. 2 hours was taken for the sulfuric acid concentration to decrease from 3% to 0.3%.

The concentration of sulfuric acid in the anode water bath increased in proportion to the electrolysis time, which was contrary to that in the cathode water bath. Specifically, the concentration of sulfuric acid in the anode water bath was 10.5% (110 g/L) at the initial stage of electrolysis but increased to 27.9% at 5 h after electrolysis, 29.9% at 6 h after electrolysis, and 31.1% at 7 h after electrolysis.

The set current (20 A) was maintained and the voltage was maintained at 15-20 V until the sulfuric acid concentration of the hydrolyzate reached ~7% (for ~5 h after electrolysis). However, the current was maintained at 20 A but the voltage increased to 29 V at ~6 h, at which the sulfuric acid concentration was reduced to 3%. When the sulfuric acid concentration was reduced to 1% at ~7 h after electrolysis, the current was only 8.5 A, which was lower than the set current value, despite the application of the maximum rated voltage (30 V), and thereafter, the current was reduced to 5 A. Therefore, the use of the first sugar-acid separation tank prior to 6 h after electrolysis at which the sulfuric acid concentration of the hydrolyzate decreased in proportion to the electrolysis time and a second sugar-acid separation tank, which has a larger anion separator than the first sugar-acid separation tank, following 6 h after electrolysis at which the electrolysis rate was low is preferred for fast electrolysis.

It was also confirmed that the concentrations of sugars in the cathode water bath increased slowly in proportion to the electrolysis time and were not affected by the voltage and current changes.

PRODUCTION EXAMPLE 1

Primary and Secondary Electrolysis (in Open Electrolysis Tank+Open Electrolysis Tank)

30% sulfuric acid, 60 g/L glucose, and 20 g/L xylose were mixed and slowly stirred at 60° C. for 1 h to prepare a hydrolyzate.

As in Comparative Production Example 1, 500 mL of the hydrolyzate and 500 mL of an aqueous solution of 10% sulfuric acid were added to a cathode water bath and an anode water bath of a first sugar-acid separation tank (open electrolysis tank), respectively. Platinum electrodes having the same size (5 cm×8 cm) were immersed in the solutions in the water baths. Primary electrolysis was performed for 6 h while maintaining a current of 20 A between both electrodes. At this time, the voltage was set to a maximum of 25.0 V. Two small agitators were installed adjacent to the platinum electrodes in each of the cathode water bath and the anode water bath to maintain the concentrations of sugars and sulfuric acid at constant levels.

After completion of the primary electrolysis, 500 mL of an aqueous solution of 10% sulfuric acid and the hydrolyzate, from which the aqueous sulfuric acid solution had been separated in the first sugar-acid separation tank, were added to an anode water bath and a cathode water bath of a second sugar-acid separation tank (open electrolysis tank) having the same structure as the first sugar-acid separation tank. 100 mL of water was added to the hydrolyzate such that the sugar concentration was reduced to 122 g/L. Secondary electrolysis was performed by opening a maximum rated voltage of 30 V to both electrodes and allowing a fixed current of 20 A to flow in a constant current mode.

TEST EXAMPLE 2

Measurement of Changes in Concentration of Sugars and Sulfuric Acid During Electrolysis in Production Example 1

FIG. 5a shows changes in the concentration of sulfuric acid in the anode water bath and the cathode water bath during primary electrolysis in Production Example 1. FIG. 5b shows changes in voltage and current applied to the cathode and the anode with varying concentrations of sulfuric acid during primary electrolysis in Production Example 1. FIG. 5c shows time-dependent changes in the concentration of sugars in the hydrolyzate in the cathode water bath during primary electrolysis in Production Example 1.

FIG. 6a shows changes in the concentration of sulfuric acid in the anode water bath and the cathode water bath during secondary electrolysis in Production Example 1. FIG. 6b shows changes in voltage and current applied to the cathode and the anode with varying concentrations of sulfuric acid during secondary electrolysis in Production Example 1. FIG. 6c shows changes in the concentration of sugars in the hydrolyzate in the cathode water bath with time during secondary electrolysis in Production Example 1.

As shown in FIGS. 5a to 5c, the voltage was maintained at 20 V or less (usually 15-17 V) during primary electrolysis at 20 A for 6 h. The concentration of sulfuric acid in the cathode water bath was 25.7% (288 g/L) at the initial stage of electrolysis but was reduced to 2.9% in proportion to the electrolysis time. In contrast, the concentration of sulfuric acid in the anode water bath increased from 10% to about 31% (356 g/L) in proportion to the electrolysis time. The sugar concentration of the cathode water bath increased from 121.3 to 153.3 g/L in proportion to the electrolysis time.

As shown in FIGS. 6a to 6c, when water was added to reduce the concentration of sugars in the cathode water bath during secondary electrolysis, the sulfuric acid concentration was lowered to ~2.5% and the electrical conductivity of the aqueous solution was thus lowered. As the electrolysis proceeded, sulfuric acid moved from the anode water bath to the cathode water bath. As a result, the concentration of sulfuric acid in the anode water bath was further lowered, resulting in slow migration of sulfate ions with the passage of electrolysis time.

During secondary electrolysis, a current of 20 A was maintained at a voltage of 30 V or less until the sulfuric acid concentration of the hydrolyzate in the cathode water bath reached 1% (for 1 h after electrolysis), and thereafter, the current was reduced to about 12 A at 2 h, at which the sulfuric acid concentration was reduced to ~0.3%, despite the application of the maximum rated voltage (30 V) and the migration velocity of sulfate ions was also lowered. 3 h after electrolysis, the sugar concentration of the hydrolyzate increased from 122.0 g/L to 128.5 g/L and the sulfuric acid concentration was reduced to ~0.1%.

In the present invention, the voltage applied between the anode and the cathode could be maintained lower until the concentration of sulfuric acid in the cathode water bath reached a predetermined value when the hydrolyzate and the aqueous sulfuric acid solution were stirred in the cathode water bath and the anode water bath, respectively, than when stirring was not performed. Even when the concentration of sugars in the cathode water bath was high, a smooth migration of sulfate ions was observed. When there was a very large difference in sulfuric acid concentration between the anode water bath and the cathode water bath, particularly, when electrolysis was performed at an extremely high concentration of sulfuric acid for a long time, the anion separator was corrugated and deformed. This problem could be solved by performing the electrolysis in divided steps, i.e. primary electrolysis and secondary electrolysis, so that an excessive increase in the concentration of sulfuric acid in the anode water bath and long electrolysis at a high concentration of sulfuric acid were prevented. In addition, when secondary electrolysis separately from primary electrolysis was performed by adding water to the cathode water bath to reduce the concentration of sugars, the carbonization of sugars on the cathode surface could be prevented despite the application of a high voltage at a low concentration of sulfuric acid.

PRODUCTION EXAMPLE 2

Primary and Secondary Electrolysis (in Open Electrolysis Tank+Closed Electrolysis Tank)

In the same manner as in Production Example 1, 30% sulfuric acid, 60 g/L glucose, and 20 g/L xylose were mixed and slowly stirred at 60° C. for 1 h to prepare a hydrolyzate. Primary electrolysis was performed in a first sugar-acid separation tank (open electrolysis tank) equipped with an anion separator (diameter of circular liquid contact side: 45 mm, NEOSEPTA-AMX anion-exchange membrane, ASTOMS) and small agitators in a constant current mode for 6 h while maintaining a current of 20 A. After completion of the primary electrolysis, concentrated sulfuric acid was separated from the anode water bath and the hydrolyzate was diluted with water to a sugar concentration of 128 g/L in the cathode water bath. The sulfuric acid concentration of the hydrolyzate was measured to be 2.7%.

The dilute hydrolyzate was transferred to a hydrolyzate storage tank and an aqueous solution of 10% sulfuric acid was filled in a sulfuric acid storage tank. Thereafter, the dilute hydrolyzate and the aqueous sulfuric acid solution were supplied to a cathode water bath and an anode water bath of a second sugar-acid separation tank (closed electrolysis tank) at the same flow rate of 120 ml/min, respectively. The closed electrolysis tank used the same kind of anion separator (diameter of circular liquid contact side: 125 mm, NEOSEPTA-AMX anion-exchange membrane, ASTOMS) applied to the open electrolysis tank for primary sugar-acid separation. Considering the total area of holes of PTFE films (247a of FIG. 3b) supporting the anion separator was 56.9 cm$^2$, the anion separator was predicted to have a liquid contact area of 56.9-122.7 cm$^2$. Circular platinum plates, each having the same size as the anion separator (inner diameter: 125 mm), were used as an anode and a cathode. Each electrode had 5 holes (diameter: 3 mm) formed along the arc in the lower end portion thereof. The solution supplied to the rear side of each electrode moved to the front side of the electrode (facing the anion separator) through the holes, electrolyzed, and discharged, together with a gas (hydrogen or oxygen), through a discharge port formed on the front portion. Secondary electrolysis was performed by opening a maximum rated voltage of 30 V between the anode and the cathode and allowing a current of 20 A to flow in a constant current mode. Portions of the aqueous sulfuric acid solution and the hydrolyzate were sampled at the discharge ports formed on the anode water bath and the cathode water bath with the passage of electrolysis time. The sulfuric acid concentrations of the solutions were analyzed.

TEST EXAMPLE 3

Measurement of Changes in Concentration of Sugars and Sulfuric Acid During Electrolysis in Production Example 2

FIG. 7a shows changes in the concentration of sulfuric acid in the anode water bath and the cathode water bath during secondary electrolysis in the closed sugar-acid separation tank while circulating the aqueous sulfuric acid solution between the anode water bath and the aqueous sulfuric acid solution storage tank and the hydrolyzate between the cathode water bath and the hydrolyzate storage tank in Production Example 2. FIG. 7b shows changes in voltage and current applied to the cathode and the anode of the closed sugar-acid separation tank during secondary electrolysis in Production Example 2.

As shown in FIGS. 7a and 7b, the current density was lowered at the anion separator of the closed sugar-acid separation tank whose liquid contact area was 3.6-7.7 times larger than that of the anion separator of the sugar-acid separation tank used in Production Example 1. As a result, ~2.5 hours were taken until the sulfuric acid concentration was reduced to ≤0.1%. The separation time was shortened by ~20% compared to that (3 h) in Production Example 1 and the voltage increased at a lower rate than that in Production Example 1. When the electrolysis was finished, no carbonization was observed on the surface of the cathode in the closed electrolysis tank.

In the present invention, electrolysis was performed while stirring the aqueous sulfuric acid solution and the hydrolyzate in the respective storage tanks and circulating the aqueous sulfuric acid solution and the hydrolyzate between the corresponding storage tanks and water baths. The same effects of electrolysis could be obtained as those of electrolysis while stirring the aqueous sulfuric acid solution and the hydrolyzate in the open electrolysis tank. The use of the large anion separator was confirmed to lower the current density of the separator. This reduces the applied voltage, contributing to high energy efficiency and rapid acid separation.

PRODUCTION EXAMPLE 3

Primary Electrolysis Using the Aqueous Sulfuric Acid Solution Recovered in Secondary Electrolysis In the same manner as in Production Example 1, 30% sulfuric acid, 60 g/L glucose, and 20 g/L xylose were mixed and slowly stirred at 60° C. for 1 h to prepare a hydrolyzate. 500 ml of the hydrolyzate and 500 ml of the aqueous solution of 12.2% (129 g/L) sulfuric acid collected as a result of the second sugar-acid separation (using the closed electrolysis tank) in Production Example 2 were added to a cathode water bath and an anode water bath of a first sugar-acid separation tank (open electrolysis tank), respectively. The first sugar-acid separation tank was equipped with small agitators and the same kind of anion separator (diameter of circular liquid contact side: 45 mm, NEOSEPTA-AMX anion-exchange membrane, ASTOMS) used in Production Example 1. Platinum electrodes were immersed in the solutions in the water baths. Primary electrolysis was performed in a constant current mode for 6 h while maintaining a current at 20 A between both electrodes. The voltage was set to a maximum of 25.0 V. Stirring was performed with the small agitators in the cathode and anode water baths to maintain uniform concentrations of sugars and sulfuric acid in the water baths, respectively.

TEST EXAMPLE 4

Measurement of Sugar and Sulfuric Acid Concentrations During Electrolysis in Production Example 3

FIG. 8a shows changes in the concentration of sulfuric acid in the anode water bath and the cathode water bath during primary electrolysis in Production Example 3. FIG. 8b shows changes in voltage and current applied to the cathode and the anode with varying concentrations of sulfuric acid during primary electrolysis in Production Example 3.

As shown in FIGS. 8a and 8b, the voltage was maintained at 21 V or less (usually 14-17 V) during primary electrolysis at 20 A for 6 h. The sulfuric acid concentration of the hydrolyzate in the cathode water bath was 25.8% (289 g/L) at the initial stage of electrolysis and was then reduced to 3.5% (35 g/L) in proportion to the electrolysis time. In contrast, the concentration of sulfuric acid in the anode water bath was increased from 12.2% to 32.6% (377 g/L) in proportion to the electrolysis time. The use of the aqueous solution of 12.2% sulfuric acid, which was recovered after secondary electrolysis, in the anode water bath of the primary electrolysis tank showed similar results to the use of a new aqueous solution of 10% sulfuric acid for primary electrolysis in Production Example 1 (FIGS. 5a and 5b). These results conclude that the aqueous solution of ~12% sulfuric acid collected recovered after secondary electrolysis can be partially or entirely utilized in the anode water bath for primary electrolysis.

EXAMPLE 1

1 kg of a finely-divided waste wood powder (43 wt % cellulose, 25% hemicellulose, 21% lignin, and 11% other components including ash) having a water content of 10 wt % was mixed with an aqueous solution of 70% sulfuric acid (concentrated sulfuric acid) in a weight ratio of 1:3 in a 5-liter pretreatment reactor made of a fiber reinforced polymer (FRP). When the mixture was slowly stirred for 10 min, the waste wood disappeared. The pretreatment was stopped when a sticky black viscous slurry was observed with a temperature increase to 45-50° C. The slurry was transferred to a 20-liter hydrolysis tank made of glass-lined carbon steel connected to the bottom of the pretreatment tank through a PTFE ball valve installed under the pretreatment tank, while water was added to the pretreatment tank. The water was added in such an amount that the sulfuric acid concentration of the slurry was 25%. Hydrolysis was performed with slow stirring for 1 h while maintaining the temperature of the slurry at 80° C. using a jacket heater of the hydrolysis tank. After completion of the reaction, the hydrolyzate and solids were transferred to a solid-liquid separation tank made of FRP through a PTFE ball valve installed under the hydrolysis tank. The mixture of the hydrolyzate and solids was passed through a polypropylene cloth filter installed on a vacuum trap to remove the solids. 8 liter of the brown hydrolyzate containing the acid solution was collected in the glass trap.

The hydrolyzate was analyzed to contain 244 g/L sulfuric acid, 43 g/L glucose, and 24 g/L xylose.

500 mL of the hydrolyzate and 500 mL of an aqueous solution of 10% sulfuric acid were added to a cathode water bath and an anode water bath of the same type of first sugar-acid separation tank (open electrolysis tank) used in Production Example 1, respectively. Platinum electrodes (size: 5 cm×8 cm) were immersed in the aqueous solutions. Primary electrolysis was performed in a constant current mode for 6 h while allowing a current of 20 A to flow between both electrodes. At this time, the voltage was set to a maximum of 25.0 V. Two small DC motor-driven low-speed agitators were installed adjacent to the platinum electrodes of each of the cathode water bath and the anode water bath to maintain constant concentrations of sugars and sulfuric acid in the water baths.

After completion of the primary electrolysis, 500 mL of an aqueous solution of 10% sulfuric acid and the hydrolyzate, from which the aqueous sulfuric acid solution had been separated in the first sugar-acid separation tank, were added to an anode water bath and a cathode water bath of a second sugar-acid separation tank having the same structure as the first sugar-acid separation tank. Secondary electrolysis was performed by opening a maximum rated voltage of 30 V to both electrodes and allowing a fixed current of 20 A to flow in a constant current mode.

TEST EXAMPLE 5

Measurement of Sugar and Sulfuric Acid Concentrations During Electrolysis in Example 1

FIG. 9a shows changes in the concentration of sulfuric acid in the anode water bath and the cathode water bath during primary electrolysis in Example 1. FIG. 9b shows time-dependent changes in the concentration of the hydrolyzate in the cathode water bath during primary electrolysis in Example 1.

FIG. 10a shows changes in the concentration of sulfuric acid in the anode water bath and the cathode water bath during secondary electrolysis in Example 1. FIG. 10b shows time-dependent changes in the concentration of the hydrolyzate in the cathode water bath during secondary electrolysis in Example 1.

As shown in FIGS. 9a and 9b, 6 h after primary electrolysis, the concentration of sulfuric acid in the cathode water bath was lowered to 25 g/L, the concentration of glucose in the cathode water bath increased to 50 g/L, and the concentration of xylose in the cathode water bath increased to 29 g/L.

A constant current operation was possible at 20 A for 6 h. At this time, the voltage was maintained at 25 V or less.

As shown in FIGS. 10a and 10b, 1 h after secondary electrolysis, a current of 20 A flowed but a maximum rated voltage of 30 V was reached. 2 h after secondary electrolysis, the current was reduced to 10 A or less, the concentration of sulfuric acid in the cathode water bath was lowered to 0.4%, and the sugar concentration increased to 90 g/L or more. 4 h after secondary electrolysis, the concentration of sulfuric acid in the cathode water bath was reduced to 0.03% (0.34 g/L) and the sugar concentration increased to about 95 g/L. Even when the secondary electrolysis was completed, the original surface of the platinum electrode of the cathode water bath was maintained. That is, no carbonization of sugars was observed despite the increased electrode temperature.

COMPARATIVE EXAMPLE 1

SMB Columns

An SMB system including four 2.5-inch polyvinyl chloride (PVC) vertical columns (outer diameter: 66.3 mm, length: 580 mm) filled with a resin (DOWEX(R) 50WX2-200 (100-200 mesh) was constructed. Hydrolyzate supply, water supply, aqueous sulfuric acid solution discharge, and hydrolyzate discharge were allowed to proceed simultaneously in the columns. Three-way solenoid valves were installed at the inlets and outlets of all columns such that the processes were carried out sequentially in the columns.

A hydrolyzate including 5% sulfuric acid, 50 g/L glucose, and 30 g/L xylose was supplied at a rate of 9.4 mL/min and water was supplied at a rate of 40 mL/min. Each valve was operated at intervals of 1645 sec to change the passages for fluid flow. ~55 min after supply, the sulfuric acid was concentrated in the raffinate (36.0 mL/min) and discharged. ~83 min after supply, the sugars were concentrated in the extract (13.4 mL/min) and discharged.

Each SMB column was fabricated by packing a vertical column (inner diameter: 23 mm, length: 83 cm) with a resin (DOWEX(R) 50WX2-200 (100-200 mesh). The resin was prepared by cross-linking a polystyrene matrix with sulfonate group (—$SO_3^-$)— containing divinylbenzene.

TEST EXAMPLE 6

Measurement of Sugar and Sulfuric Acid Concentrations in Comparative Example 1

FIG. 11a shows time-dependent changes in the concentration of sulfuric acid, glucose, and xylose at the raffinate side from the beginning of sulfuric acid discharge in Comparative Example 1. FIG. 11b shows time-dependent changes in the concentration of sulfuric acid, glucose, and xylose at the extract side from the beginning of sugar discharge in Comparative Example 1. In FIGS. 11a and 11b, the solid lines indicate the theoretically predicted concentrations and the dots indicate the experimentally analyzed concentrations.

As shown in FIGS. 11a and 11b, sulfuric acid and the hydrolyzate were separated from each other using the SMB system in Comparative Example 1. The concentration of the hydrolyzate recovered from the extract side was similar to the theoretically predicted concentration and the sulfuric acid concentration was very low (≤0.1%). In contrast, the sulfuric acid recovered from the raffinate side had a low sugar content but its concentration was lower than the theoretically predicted concentration (12 g/L). These results are believed to be because a considerable amount of sulfuric acid remained strongly adsorbed to the resin.

Although sulfuric acid was normally recovered at the theoretically predicted concentration from the raffinate side, its concentration was as low as ~1.2%. Therefore, much energy is needed to concentrate the sulfuric acid to ~70%, which is a level suitable for reuse. The sugar concentration of the hydrolyzate recovered from the extract side was as low as ~50-70 g/L. Therefore, secondary concentration is needed to increase the efficiency of subsequent fermentation. In contrast, the sulfuric acid concentration of the hydrolyzate can be easily reduced to ≤1% and the sugar concentration can be increased to ≥95 g/L by the primary electrolysis and secondary electrolysis in Example 1. In addition, sulfuric acid can be concentrated to a minimum of at least 25% (a maximum of 356 g/L) in the anode water bath by the primary electrolysis for sugar-acid separation. Therefore, the sugar-acid separation in Example 1 facilitates the concentration of the recovered aqueous sulfuric acid solution to ~70% and the concentrated aqueous sulfuric acid solution can be reused for pretreatment. The separated hydrolyzate in the electrolysis can be utilized in the subsequent fermentation without the need for additional sugar concentration. The concentrated aqueous sulfuric acid solution (~11-12%) recovered from the anode water bath of the second sugar-acid separation tank can be utilized as the initial electrolyte in the anode water bath of the first sugar-acid separation tank. In conclusion, the aqueous sulfuric acid solution recovered after the sugar-acid separation can always maintain its sulfuric acid concentration at ≥25% and can thus be easily concentrated to a higher level.

TEST EXAMPLE 7

Measurement of Energy Consumed in the Methods of Example 1 and Comparative Example 1

1 g of biomass was pretreated and hydrolyzed to prepare an acid hydrolyzate. In accordance with the methods described in Example 1 and Comparative Example 1, the acid hydrolyzate was subjected to acid-sugar separation and the resulting hydrolyzate was concentrated to a level suitable for fermentation. Sulfuric acid was recovered, concentrated, and reused for pretreatment. The amounts of energy consumed for acid-sugar separation, sulfuric acid concentration, and sugar concentration were calculated using the commercial software (PRO-II ver.8). The results are shown in Table 1.

TABLE 1

|  | Amount of energy consumed for acid-sugar separation (kcal) | Amount of energy consumed for sulfuric acid concentration (kcal) | Amount of energy consumed for sugar concentration (kcal) | Total amount of energy consumed (kcal) |
|---|---|---|---|---|
| Example 1 | $41.30 \times 10^3$ | $2.29 \times 10^3$ | $0.10 \times 10^3$ | $43.69 \times 10^3$ |
| Comparative Example 1 | 0 | $95.92 \times 10^3$ | $0.18 \times 10^3$ | $96.10 \times 10^3$ |

As can be seen from the results in Table 1, the amount of energy required in the method of Example 1 was less than half of that required in the method of Comparative Example 1. The energy saving effect is more significant taking into consideration the cooling energy required during distillation for sulfuric acid concentration. The method of Example 1 enables the preparation of a concentrated hydrolyzate, eliminating the need for an additional process for hydrolyzate concentration.

The use of the large anion separator for electrolysis in the method of Example 1 reduces the current density at the anion separator. When the distance between the anode and the cathode is decreased and effective stirring is performed, the voltage applied between the electrodes can be slightly lowered, contributing to energy saving. Since no sugars remain in the separated aqueous sulfuric acid solution, no sugar loss is caused. The recovered aqueous sulfuric acid solution can be easily concentrated to ≥70%. Furthermore, the apparatus used in Example 1 is simpler in structure and operation than that used in Comparative Example 1 including columns, 3-way supply valves, and 3-way discharge valves, which require sophisticated operations.

EXAMPLE 2

In this example, the open electrolysis tank used in Production Example 2 was omitted, and sulfuric acid was separated from the hydrolyzate prepared in Example 1 using a rectangular closed electrolysis tank instead of the circular closed electrolysis tank. A rectangular anion separator (width: 125 mm, length: 250 mm, NEOSEPTA-AMX anion-exchange membrane, ASTOM) supported by a PVC guide in the form of a lattice was used in the rectangular closed electrolysis tank. One side of the anion separator was predicted to have a liquid contact area of 300 $cm^2$. Rectangular DSA type electrode plates (thickness: 3 mm) having the same size (width: 125 mm, length: 250 mm) as the anion separator were used as an anode and a cathode. Holes were formed in the lower portion of each electrode. The solution fed to the rear side of each electrode was homogeneously supplied to the front side of the electrode through the holes. In the compartment of each of the cathode and the anode separated by the anion separator, the solution is sprayed on the front side of the electrode (facing the anion separator) through the lower portion, electrolyzed while ascending, and discharged, together with a gas (hydrogen in a cathode water bath or oxygen in an anode water bath), through a discharge port formed on the front portion.

Each of the distance between the anode and the anion separator and the distance between the cathode and the anion separator was adjusted to 3 mm. That is, the anode and the cathode were maintained at a distance of 6 mm.

The solution in the anode water bath and the solution in the cathode water bath were supplied at the same rate of 120 mL/min using pumps installed in the respective lines. The electrolyzed solution in the anode water bath, together with oxygen, was discharged and circulated to a sulfuric acid solution storage tank. The electrolyzed solution in the cathode water bath, together with hydrogen, was discharged and circulated to a hydrolyzate storage tank.

A double pipe heat exchanger was installed in the line for the transfer of the sulfuric acid solution discharged from the anode water bath of the closed electrolysis tank to reduce the temperature of the sulfuric acid solution to ≤50° C. A double pipe heat exchanger was installed in the line for the transfer of the hydrolyzate discharged from the cathode water bath of the closed electrolysis tank to reduce the temperature of the hydrolyzate to ≤50° C. Primary electrolysis was performed by opening a rated voltage to a maximum of 7.5 V and allowing a current of 100 A to flow in a constant current mode. Portions of the aqueous sulfuric acid solution and the hydrolyzate were sampled at discharge ports formed on the anode water bath and the cathode water bath with the passage of electrolysis time. The sulfuric acid concentrations of the solutions were analyzed.

TEST EXAMPLE 8

Measurement of Sugar and Sulfuric Acid Concentrations During Electrolysis in Example 2

FIG. 12a shows changes in the concentration of sulfuric acid in the anode water bath and the cathode water bath during primary electrolysis in Example 2. FIG. 12b shows changes in voltage and current applied to the cathode and the anode with varying concentrations of sulfuric acid during primary electrolysis in Example 2. FIG. 12c shows time-dependent changes in the concentration of the hydrolyzate in the cathode water bath during primary electrolysis in Example 2.

As shown in FIGS. 12a to 12c, electrolysis was performed at 100 A for 4 h while maintaining a small distance between the cathode and the anode and circulating the solutions. During the electrolysis, the voltage was maintained at <7.5 V (usually 4.7-5.5 V), and the sulfuric acid concentration of the hydrolyzate in the cathode water bath was 24.8% (276 g/L) at the initial stage and decreased to 1.6% (15.9 g/L) in proportion to the electrolysis time. In contrast, the concentration of sulfuric acid in the anode water bath increased from 3.0% (31.1 g/L) to 20.2% (253 g/L) in proportion to the electrolysis time. 4 h after electrolysis, the sulfuric acid concentration of the hydrolyzate in the cathode water bath was reduced and the electrical conductivity of the solution was raised. The primary sugar-acid separation was stopped when the voltage reached 7.5 V. The operation voltage was reduced by maintaining a small distance between the anode and the cathode, the maximum temperature of the sulfuric acid solution was maintained at ≤50° C. by installing a double pipe heat exchanger in the line for the transfer of the sulfuric acid solution discharged from the anode water bath of the electrolysis tank, and the maximum temperature of the hydrolyzate was maintained at ≤50° C. by installing a double pipe heat exchanger in the line for the transfer of the hydrolyzate discharged from the cathode water bath of the electrolysis tank. Due to the reduced operation voltage and the lowered temperatures of the solutions, sugars were prevented from being carbonized resulting from the temperature rise during electrolysis.

EXPLANATION OF REFERENCE NUMERALS

100: Bioenergy production apparatus
110: Pretreatment tank
120: Hydrolysis tank
130: Solid-liquid separation tank
140: First sugar-acid separation tank (Open electrolysis tank)
150: Second sugar-acid separation tank
160: Neutralization tank
170: Fermentation tank
a: Fourth acid solution return line
b: First acid solution supply line
c: Solid discharge line
141: Anode water bath
142: Cathode water bath
143: Anode
144: Cathode
145: Anion separator
145': Anion separator support
146: Agitator
147: Cooling coil
148: Acid solution supply line
149: Hydrolyzate supply line
A: Oxygen vent port
B: Hydrogen vent port
240: Closed electrolysis tank
241: Anode water bath
242: Cathode water bath
243: Anode
243a: Electrode holes for fluid flow
243b: Electrode ear for power connection
244: Anode power connector
245: Cathode
246: Cathode power connector
247: Anion separator
247a: Anion separator support
248: Sulfuric acid solution circulation pump
249: Sulfuric acid solution storage tank
250: Cooling jacket of sulfuric acid solution storage tank
251: Agitator of sulfuric acid solution storage tank
252: Thermometer sheath of sulfuric acid solution storage tank
253: Oxygen vent port
254: Discharge valve of sulfuric acid solution storage tank
255: Hydrolyzate circulation pump
256: Hydrolyzate storage tank
257: Cooling jacket of hydrolyzate storage tank
258: Agitator of hydrolyzate storage tank
259: Thermometer sheath of hydrolyzate storage tank
260: Hydrogen vent port
261: Discharge valve of sulfuric acid solution storage tank
262: Polypropylene woven filter

INDUSTRIAL APPLICABILITY

According to the apparatus and method of the present invention, biomass is pretreated with a concentrated acid solution to extract polysaccharide structures from the biomass, the sugar components are hydrolyzed, the acid hydrolyzate is electrolyzed into a hydrolyzate and an acid solution, and the hydrolyzate is fermented to produce bioalcohol as bioenergy. In addition, the acid solution is recovered, concentrated to the same level as the concentrated acid solution used for the pretreatment, and reused for bioenergy production.

What is claimed is:

1. An apparatus for bioenergy production using a regenerated acid solution, comprising:
   a pretreatment tank where biomass and a first acid solution are stirred to extract sugar components from the biomass, the pretreatment tank connected to;
   a hydrolysis tank where the pretreated mixture transferred from the pretreatment tank is hydrolyzed to produce an acid hydrolyzate and solids, the hydrolysis tank connected to;
   a solid-liquid separated tank where the acid hydrolyzate and solids are separated, the solid-liquid separation tank connected to;
   a first sugar-acid separation tank where the acid hydrolyzate transferred from the solid-liquid separation tank is separated into a second acid solution and a first hydrolyzate, the first sugar-acid separation tank connected to;
   a second sugar-acid separation tank where the first hydrolyzate transferred from the first sugar-acid separation tank is separated into a third acid solution and a second hydrolyzate, the second sugar-acid separation tank connected to;
   a fermentation tank where the second hydrolyzate transferred from the second sugar-acid separation tank is fermented to produce bioenergy; and
   an acid solution concentration tank where a mixture of the second acid solution transferred from the first sugar-acid separation tank and the third acid solution transferred from the second sugar-acid separation tank is concentrated to a higher level for reuse,
   wherein the first sugar-acid separation tank and the second sugar-acid separation tank are electrolysis tanks, each electrolysis tank comprising a cathode water bath and an anode water bath separated by an anion separator and wherein the acid hydrolyzate is added to the cathode water bath and water or an acid solution is added to the anode water bath.

2. The apparatus according to claim 1, further comprising an acid solution return line for returning a fourth acid solution concentrated in the acid solution concentration tank to the pretreatment tank.

3. The apparatus according to claim 2, wherein the first, second, third, and fourth acid solutions are aqueous sulfuric acid solutions.

4. The apparatus according to claim 2, wherein the first acid solution and the fourth acid solution are aqueous solutions of 50 to 97% sulfuric acid.

5. The apparatus according to claim 1, further comprising a neutralization tank where the second hydrolyzate transferred from the second sugar-acid separation tank is neutralized with an alkaline substance before fermentation.

6. The apparatus according to claim 5, wherein the alkaline substance is an aqueous solution of at least one alkali selected from the group consisting of calcium hydroxide, calcium oxide, calcium carbonate, calcium bicarbonate, sodium hydroxide, sodium carbonate, sodium bicarbonate, potassium hydroxide, potassium carbonate, and potassium bicarbonate.

7. The apparatus according to claim 1, wherein the third acid solution separated in the second sugar-acid separation tank is added to the first sugar-acid separation tank.

8. The apparatus according to claim 1, wherein each of the anode water baths and the cathode water baths of the first and second sugar-acid separation tanks comprises a low-speed agitator.

9. The apparatus according to claim 1, wherein each of the anode water baths of the first and second sugar-acid separation tanks comprises a cooling coil.

10. The apparatus according to claim 1, wherein the anion separator of the second sugar-acid separation tank has a size 1 to 8 times larger than that of the anion separator of the first sugar-acid separation tank.

11. The apparatus according to claim 1, wherein each of the first and second sugar-acid separation tanks comprises an acid solution storage tank to which an acid solution obtained after sugar-acid separation is transferred and a hydrolyzate storage tank to which a hydrolyzate obtained after sugar-acid separation is transferred, the two storage tanks being provided separately from the electrolysis tank.

12. The apparatus according to claim 1, wherein each of the first and second sugar-acid separation tanks comprises an anode and a cathode, the anode has a plurality of holes in the lower portion thereof, the cathode has a plurality of holes in the lower portion thereof, the acid solution is supplied and discharged through a supply port and a discharge port, respectively, the hydrolyzate is supplied and discharged through a supply port and a discharge port, respectively, and the supply ports are opposite to the discharge ports through the perforated anodes and cathodes.

13. The apparatus according to claim 1, wherein a voltage applied to each of the first sugar-acid separation tank and the second sugar-acid separation tank is maintained at 30 V or less.

14. The apparatus according to claim 1, wherein the first hydrolyzate is treated in the first sugar-acid separation tank such that the sugar concentration of the second hydrolyzate is from 70 to 150 g/L.

15. The apparatus according to claim 1, wherein the second hydrolyzate is treated in the second sugar-acid separation tank such that the acid concentration of the second hydrolyzate is 1% or less.

16. The apparatus according to claim 1, wherein the biomass is herbal biomass, woody biomass, starchy biomass or seaweed biomass or is derived from organic waste resources.

17. The apparatus according to claim 1, wherein the hydrolyzed sugars are selected from the group consisting of glucose, xylose, galactose, fructose, and arabinose.

* * * * *